(12) United States Patent
Mogul

(10) Patent No.: US 11,020,319 B2
(45) Date of Patent: Jun. 1, 2021

(54) TAMPER-RESISTANT PILL DISPENSER FOR CONTROLLED MEDICINAL OR NUTRITIONAL DOSAGE

(71) Applicant: Jamil Mogul, Santa Clara, CA (US)

(72) Inventor: Jamil Mogul, Santa Clara, CA (US)

( * ) Notice: Subject to any disclaimer, the term of this patent is extended or adjusted under 35 U.S.C. 154(b) by 0 days.

(21) Appl. No.: 16/787,011

(22) Filed: Feb. 10, 2020

(65) Prior Publication Data
US 2020/0253829 A1 Aug. 13, 2020

Related U.S. Application Data

(60) Provisional application No. 62/803,501, filed on Feb. 10, 2019, provisional application No. 62/804,224, filed on Feb. 12, 2019, provisional application No. 62/805,970, filed on Feb. 15, 2019.

(51) Int. Cl.
*A61J 7/04* (2006.01)
*G16H 20/13* (2018.01)

(52) U.S. Cl.
CPC ........... *A61J 7/0445* (2015.05); *A61J 7/0436* (2015.05); *A61J 7/0481* (2013.01); *G16H 20/13* (2018.01);
(Continued)

(58) Field of Classification Search
CPC ...... A61J 7/0445; A61J 7/0481; A61J 7/0436; A61J 2200/30; A61J 2200/70; G16H 20/13
See application file for complete search history.

(56) References Cited

U.S. PATENT DOCUMENTS

| 4,653,009 A | * | 3/1987 | Brown | G07B 3/02 |
| | | | | 194/200 |
| 5,812,410 A | * | 9/1998 | Lion | G07F 17/0092 |
| | | | | 221/9 |

(Continued)

*Primary Examiner* — Michael Collins
(74) *Attorney, Agent, or Firm* — Hamrick IP-Law Office; Claude A. S. Hamrick

(57) ABSTRACT

A tamper-resistant pill and/or capsule dispenser for attachment to an electronic control and communication unit including inter alia, an electric actuator mechanism, a microprocessor, a graphical user interface and a communications unit, the dispenser including sensors operative under control of said electronic control and communication unit to monitor and dispense prescribed dosages of medications or vitamin supplements in pill and/or capsule form and help control, track and maintain a record of pills and/or capsules dispensed to a patient to ensure that the dispensed product is not improperly removed from or replaced in the dispenser, said dispenser comprising:

a generally cylindrical housing having an open top, and a generally closed bottom, except for a pill dispensing opening formed in a lower side portion of the cylindrical housing; a cylindrical sleeve open at its top end and closed at its bottom end, said sleeve being eccentrically disposed within said cylindrical housing and away from the side of said cylindrical housing having said pill dispensing opening, said sleeve being affixed at its bottom end to the bottom end of said cylindrical housing and having an open, longitudinally extending slot formed in the side thereof opposite said pill dispensing opening; an axially rotatable cylinder disposed within said housing, said cylinder having a helical indented groove formed in the outer cylindrical surface thereof, said groove extending from a point proximate an upper end of said cylinder to a point proximate a lower end of said cylinder, said groove being adapted to slidably carry pills and/or capsules to be sequentially passed through said first pill exiting aperture, said axially rotatable cylinder having a (Continued)

coupling socket formed in its upper end for driving engagement with said electric actuator mechanism: and a tubular slide slidably disposed about said sleeve and carrying a pill pin for slidably engaging pills and/or capsules disposed in said helical indented groove as said electric actuator mechanism causes said axially rotatable cylinder to rotate and dispense pills and/or capsules out of said pill dispensing opening.

3 Claims, 22 Drawing Sheets

(52) U.S. Cl.
CPC ........ *A61J 2200/30* (2013.01); *A61J 2200/70* (2013.01)

(56) References Cited

U.S. PATENT DOCUMENTS

| | | | | |
|---|---|---|---|---|
| 7,949,426 B2* | 5/2011 | Handfield | ............... | G07F 11/24 |
| | | | | 700/236 |
| 2006/0201963 A1* | 9/2006 | Sines | ................. | B65D 83/0005 |
| | | | | 221/279 |
| 2008/0149661 A1* | 6/2008 | Sines | .................... | B65D 21/08 |
| | | | | 221/279 |
| 2010/0318218 A1* | 12/2010 | Muncy, Jr. | ......... | B65D 83/0409 |
| | | | | 700/220 |
| 2013/0256331 A1* | 10/2013 | Giraud | ................. | A61J 7/0418 |
| | | | | 221/1 |
| 2013/0313258 A1* | 11/2013 | Sines | .................... | B65D 81/22 |
| | | | | 220/288 |
| 2019/0307648 A1* | 10/2019 | Bartos | .................. | A61J 7/0418 |

\* cited by examiner

SECTION A-A

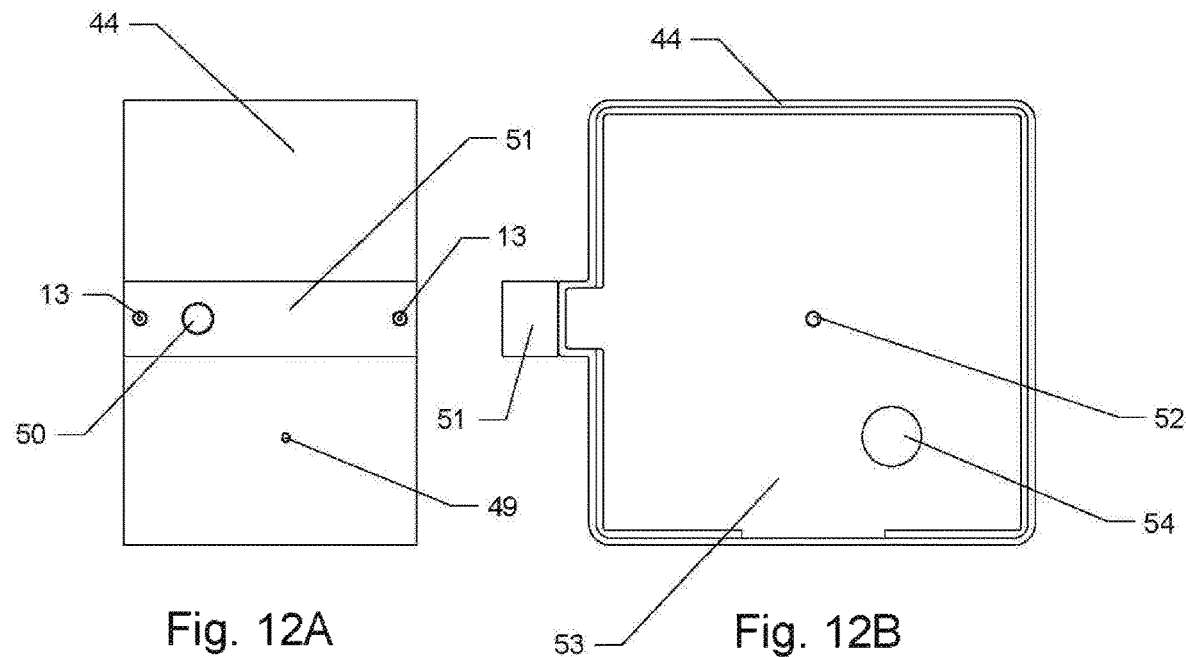
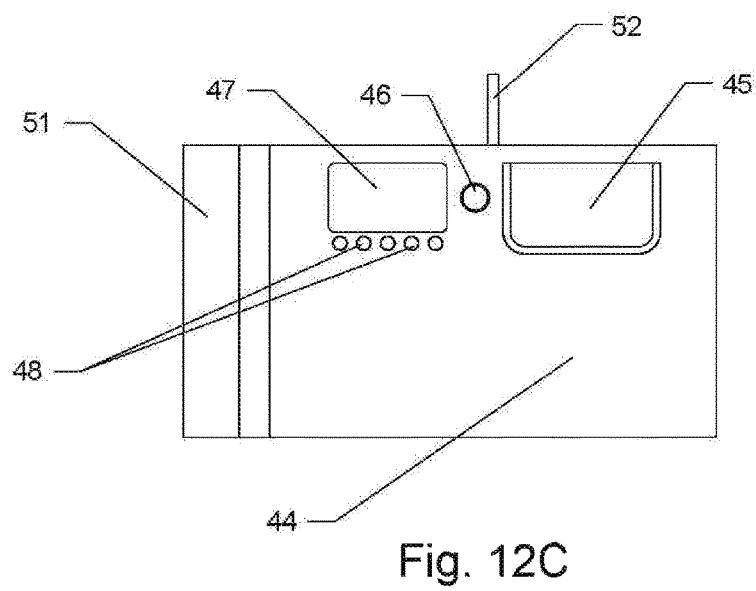

SECTION A-A

SECTION A-A

SECTION C-C

SECTION B-B

SECTION A-A

TAMPER-RESISTANT PILL DISPENSER FOR CONTROLLED MEDICINAL OR NUTRITIONAL DOSAGE

BACKGROUND

Field of the Invention

The present invention relates to an apparatus that contains and dispenses a dosage of medicinal or nutritional pills controllably in a metering manner for a user of the pills and that resists any tampering efforts to remove or replace the pills.

Prior Art

Prescribed, recommended or chosen medicinal or nutritional pills are commonly contained in a bottle and secured with a special bottle cap which is often child-proof. For an adolescent or adult patient who uses the pills, the bottle cap is embossed or engraved with a graphic and/or written direction on how to open the cap to retrieve the pills from the bottle. After opening the bottle cap, the patient who now has now an access to all the pills can retrieve and take a certain quantity of the pills per the prescribed or recommended dosage labeled on the bottle.

Another container of pills is in a form of a mini round or square or rectangular box with loose or captive lid that is screwed on or snapped into the box in order to secure the pills. Each of these mini boxes is color coded and/or printed with a day of the week and contains a prescribed or recommended quantity of pills for each dosage. The mini boxes are organized by loosely stacking them or press-fitting or detachably snapping them in a carrier frame. After opening the mini box lid, the patient can access, retrieve and take the pills in the mini box.

Yet another container of pills in a form of strip or disk containing mini compartments each with a loose or captive lid that is color-coded or printed with a day of the week. Each compartment contains a prescribed or recommended quantity of pills for each dosage. Several strips, each of which has seven compartments (one each day of the week), are detachably snapped together for containing a quantity of pills to be used for more than a week. In some cases, the disk can have no lids for the compartments, but it has a cover that securely protects the pills in each compartment from spilling them. The compartment lid or cover is opened to access, retrieve and take the pills in the compartment.

Still another container of pills is a mini pouch with a peelable or tearable side that is adhesive-or-heat-sealed after placing a prescribed or recommended quantity of pills for a dosage. Each mini pouch is color-coded or printed with a day and/or/time for taking pills for each dosage. Multiple mini pouches each containing a dosage of pills are provided to the user depending on daily, weekly or monthly use of the pills. A pouch is peeled or torn to access, retrieve and take the pills in the pouch.

Still another container of pills is a 7-day pill organizer & 4-times-a-day medicine holder in a cylindrical storage/travel pill box. This pill box has 7 individual daily pocketable vertically stacked carrier dishes each of which has 4 separate compartments. Each compartment is for a certain time of the day. Per their prescribed or recommended dosage, the pills are placed in each compartment that is then sealed with a plastic film. The carrier dishes are color-coded or printed with a name of the day of the week. To access, retrieve and take the pills in its compartment, the sealed film is broken manually or with a tool used by those who are unable to manually break the sealed film.

The abovementioned pill container types that are commercially and readily available in drug or vitamin stores or online department stores provide an open access to and easy retrieval of pills, affording the patient an opportunity to abuse the pills or allowing a malicious person to remove or replace the pills, causing the patient a potential harm either way.

The Problems Addressed

After medicinal pills are prescribed to a patent with a disease or supplement nutritional pills are recommended to a patient with a nutritional deficiency, there is no guaranty that the patient will adhere to the prescription instructions and take the dosages of the pills as described or directed by the doctor and/or pharmacist. There is a possibly that the patient may take underdoses or overdoses accidentally or intentionally or may even not take any recommended doses or stop taking the recommended doses in the middle of the treatment due to possibly a concern of side effects of the pills. Overdoses, underdoses or no doses at all, which may be harmful to the patient, must be controlled. But unfortunately, there exists no effective way recently to do that, especially when a patient is expected to take the doses on his/her own at home.

Various studies show that doctors have no way of knowing if their patients have followed the dosage that are recommended for an at-home use and/or that patients are found to be not fully adherent to the drug dosage. This seems to be a problem in the healthcare industry.

Providing prescribed pills in any of the abovementioned pill containers that allow easy, uncontrollable, full access to the whole weekly or monthly quantity of prescription pills has greatly contributed to abuse of pills by a patient who tends to ignore the prescription instructions or use recommendation. Or in a worst-case scenario, if the patient is addicted to the prescription pills (such opioids) or in a state of mind that compels him/her to sooth an overwhelming emotional pain or forces him/her to have suicidal tendency, he/she can easily access all the pills in any one of these containers and retrieve and take them all at once, which would be potentially harmful to him/her On the other hand, if a patient who tends to ignore the prescription instructions or use recommendation and decides not to take the dosage of the pills and dispose of the pills, this act would be also potentially harmful to him/her or complicate his/her prognosis during a follow-up visit with the physician that prescribed the pills.

A Solution to the Problems

To address the issues mentioned above, a tamper-resistant pill dispenser is designed not only to dispense incrementally prescribed pills, but also to help control, track and maintain the record of the dosage of the pills taken by a patient and also to alert the physician and/or pharmacist of any malicious removal or replacement of the pills while recording and archiving the incident as an evidence.

BRIEF SUMMARY OF THE INVENTION

In accordance with the present invention, there are three embodiments of the invention which are briefly stated below.

In its first embodiment, the pill dispenser uses a chain-sprocket and Geneva-mechanism design. A closed-loop pill ring chain formed by linked pill rings each containing a pill or pills or a packaged pill or a packaged set of pills are engaged to the idler disks and the sprocket with a Geneva drive linked with a Geneva driver in a covered housing. The sprocket is rotated via the Geneva driver spindle to achieve a translational movement of the pill ring chain, which movement results in exiting of the pill or the pills or the packaged pill or the packaged set of pills from a hole at the bottom of the housing.

To operate the pill dispenser, it is detachably attached to an operation box that has, among other items, a compartment for the dispensed pill or multiple pills and a computer-controlled electric motor couples with the Geneva driver. A mechanism, as a backup, also couples with the Geneva drive, to manually operate the pill dispenser in case of an electrical malfunction. The operation box connects to internet, controls pill dispensation and tracks and maintains the record of pill dispensation and the dosage or no dosage taken, including video files. An empty pill dispenser is replaced.

In its second embodiment, the pill dispenser uses a spiral-grooved disk with an integral spindle and with a toggle containing a pill pin that engages with the spiral groove. Pills or individually packaged pills or multiple sets of packaged pills are placed in the disk's spiral groove that can be filled to the capacity. The disk's rotation causes the pill pin to move in the groove, which movement results in exiting of the pill or the pills or the packaged pill or the packaged set of pills from a hole at the bottom of the housing.

To operate the pill dispenser, it is detachably is attached to an operation box that has, among other items, a compartment for the dispensed pill or pills and a computer-controlled electric motor and a solenoid actuator. During the attachment, the pill dispenser's housing's protruded cap's end gets broken while coupling the motor shaft with the disk's spindle. The solenoid actuator breaks the bond of the spring-loaded plug while helping open the hole for the exit of the pills or packaged pills during a rotation of the disk via the electric motor. The operation box connects to internet, controls pill dispensation and tracks and maintains the record of pill dispensation and the dosage or no dosage taken, including video files. An empty pill dispenser is replaced.

In its third embodiment, the pill dispenser has among other items, a helically grooved cylinder, a sleeve, and a pill pin that engages with the helical groove. A strip of the sleeve is slid out and pills or individually packaged pills or multiple sets of packaged pills are placed through the slot into the helical groove that can be filled to the capacity, and then the strip is slid back to close the slot. The cylinder's rotation causes the pill pin to move in the groove, which movement results in exiting of the pill or the pills or the packaged pill or the packaged set of pills from a hole at the bottom of the housing.

To operate the pill dispenser, it is detachably is attached to an operation box that has, among other items, a compartment for the dispensed pill or pills and a computer-controlled electric motor and a solenoid actuator. During the attachment, the pill dispenser's housing's protruded cap's end gets broken while coupling the motor shaft with the cylinder. The solenoid actuator breaks the bond of the spring-loaded plug while helping open the hole for the exit of the pills or packaged pills during a rotation of the cylinder via the electric motor. The operation box connects to internet, controls pill dispensation and tracks and maintains the record of pill dispensation and the dosage or no dosage taken, including video files. An empty pill dispenser is replaced.

An important advantage of the present invention is that it resists tampering efforts made by a person who may want to remove or replace the pills for their abuse by taking them in a quantity beyond the prescribed dosage or for a malicious reason to cause a harm.

Another important advantage of the present invention is that it provides documented digital information with regards to any tampering efforts, pill dispensation, and taking of prescribed dosage, any overdosage or no dosage of pills. This information is not only useful in its functional self-checks, but also in controlling the dosage and the frequency of the dosage of pills taken in order to conform with the prescription. Moreover, this information can be also used as an evidence against a person who made tampering efforts maliciously to cause a harm to the patient.

Yet another important advantage of the present invention is that it provides a history of the pill dispensation and dosage, which is helpful not only in prognosis of a disease for which the pills are prescribed, but also in learning the behavior of the patient.

Still another important advantage of the present invention is that if its tamper-resistance is somehow intentionally and forcefully overcome, it triggers an alarm and alerts, via internet, a health professional who can take an urgent action to prevent a potential overdosage of pills or to help treat the effect of overdosage if too many pills are already taken, especially when the pills are opioids that are addictive.

These and other advantages of the present invention will become apparent to those skilled in the art after a reading of the following detailed disclosure of embodiments of the present invention.

BRIEF DESCRIPTION OF THE VIEWS IN THE DRAWING

The First Embodiment

FIG. 1A, FIG. 1B and FIG. 1C show top and front plan views with a cut-away and bottom plan view, respectively, of the pill dispenser using the chain-sprocket and Geneva-mechanism design, which exhibit some of both exterior and interior parts of the pill dispenser while FIG. 1D and FIG. 1E show the top and front plan views, respectively, of the pill dispenser exhibiting only the exterior parts in accordance with the present invention. Additionally, FIG. 1F and FIG. 1G depict the top and front plan views, respectively, of the pill ring chain of the pill dispenser using the chain-sprocket and Geneva mechanism design;

FIG. 2A, FIG. 2B, FIG. 2C, and FIG. 2D depict the top, front, bottom and sectional plan views, respectively, of the pill dispenser housing of the pill dispenser using the chain-sprocket and Geneva-mechanism design;

Figure 13A:
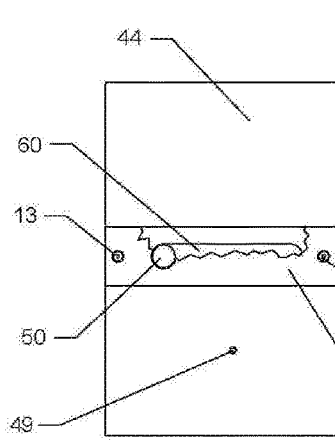
Figure 13B:
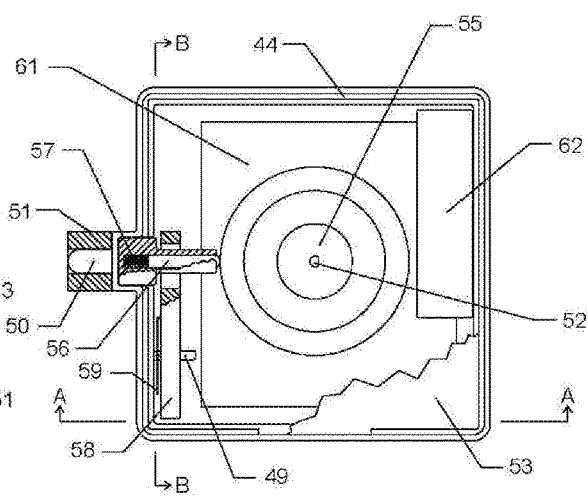
Figure 13C:
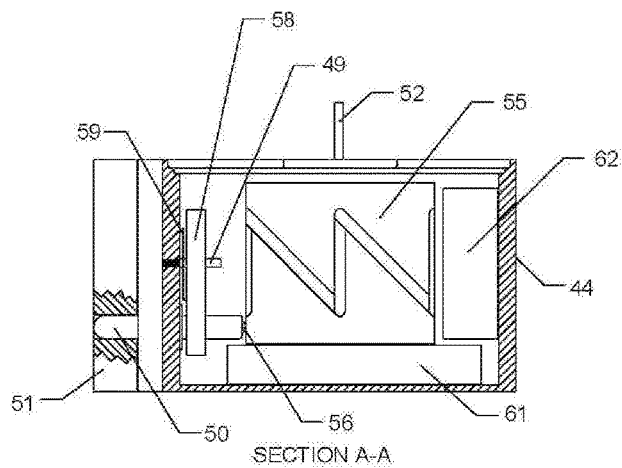
Figure 13D:
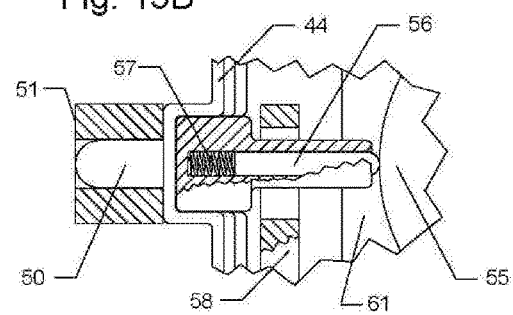
Figure 13E:
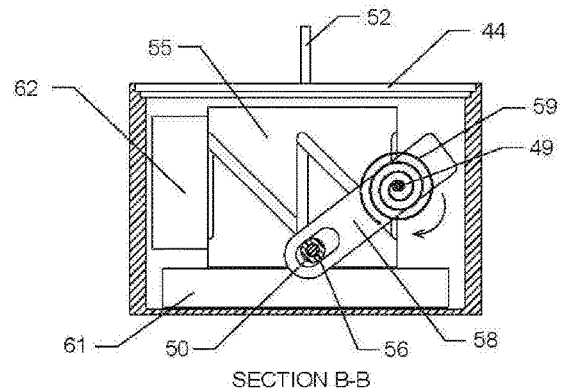

FIG. 12A, FIG. 12B and FIG. 12C depict the side, top and front plan views, respectively, of the pill dispenser operation box using the backup z-groove barrel-cam mechanism design for a manual operation, the electric motor, power supply and electronics with internet capability, display, and infrared sensors, audible alarm, light-emitting diodes and camera. These plan views exhibit the exterior parts in accordance with the present invention;

FIG. 13A and FIG. 13B show the side and top plan views with a cut-away, respectively, of the pill dispenser operation box with the mechanism locking bar while FIG. 13C and FIG. 13E depict sectional plan views of the pill dispenser operation box with the mechanism locking bar and FIG. 13D shows an enlarged view of the cut-away detailed portion of the top plan view of the pill dispenser operation box with the mechanism locking bar These plan views exhibit some of both exterior and interior parts of the pill dispenser operation box with the mechanism locking bar.

Figure 14A:
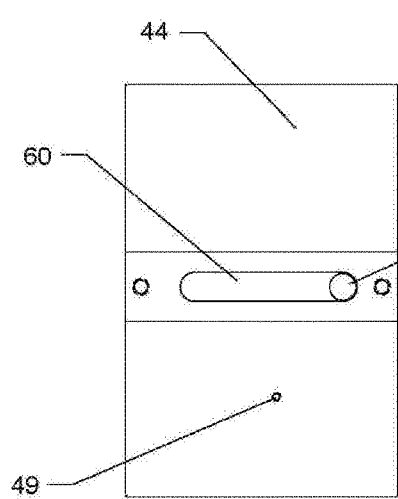
Figure 14B:
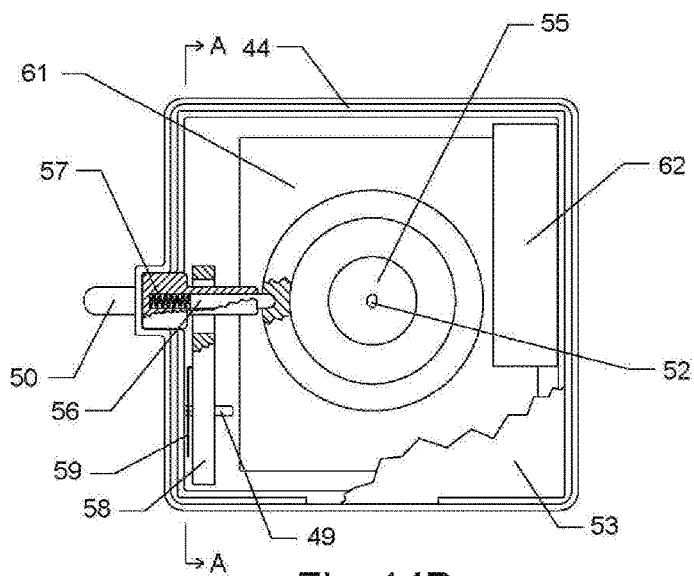
Figure 14C:
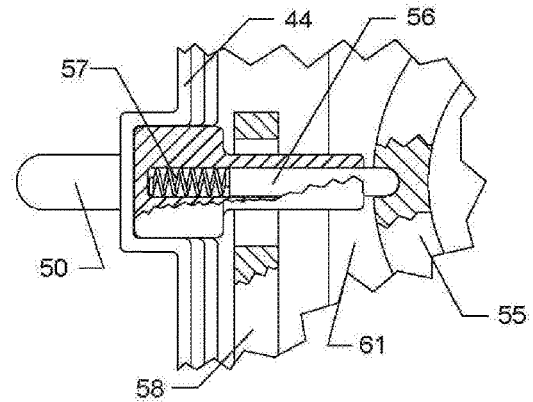
Figure 14D:
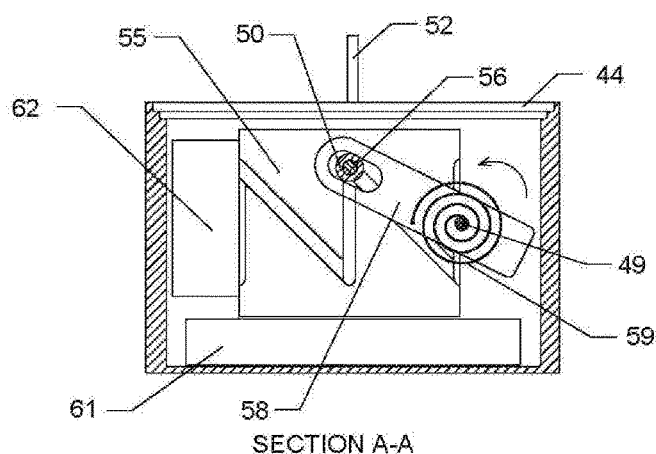

FIG. 14A and FIG. 14B depict the side plan view and the top plan view with a cut-away, respectively, of the pill dispenser operation box without the mechanism locking bar while FIG. 14D shows the sectional plan view of the pill dispenser operation box without the mechanism locking bar and FIG. 14C shows an enlarged view of the cut-away detailed portion of the top plan view of the pill dispenser operation box without the mechanism locking bar These plan views exhibit some of both exterior and interior parts of the pill dispenser operation box without the mechanism locking bar.

Figures 16A, 16B:
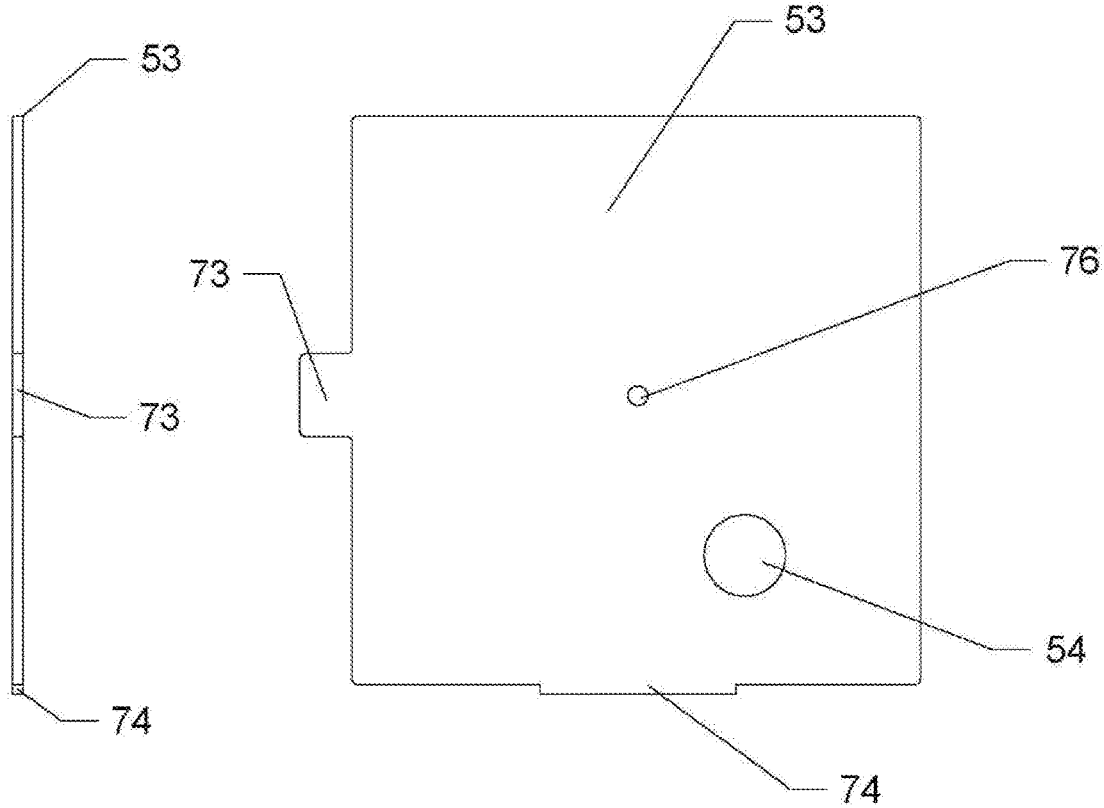
Figure 16C:
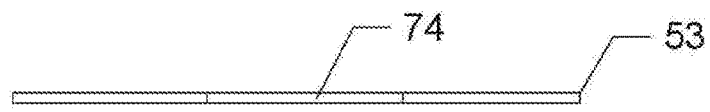
Figure 17A:
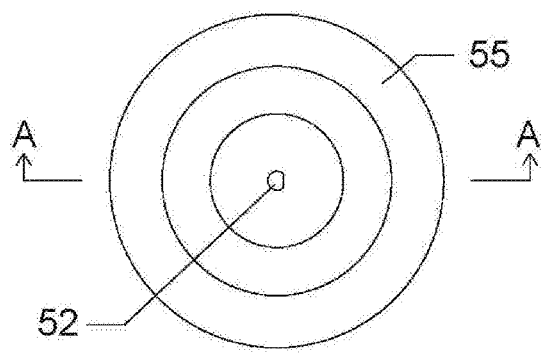
Figure 17D:
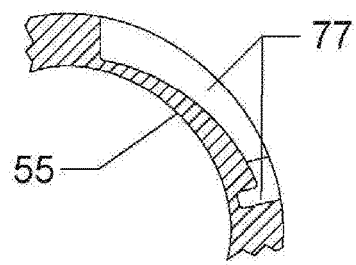
Figure 17B:
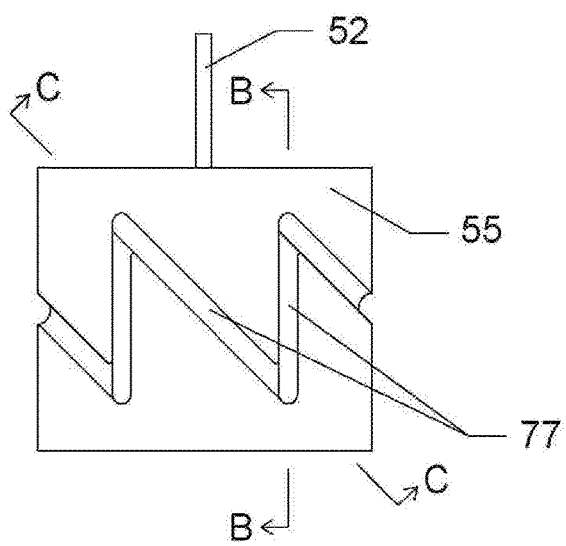
Figure 17E:
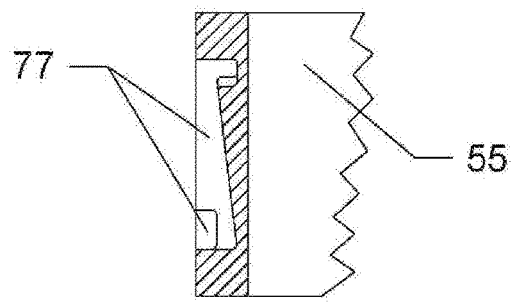
Figure 17C:
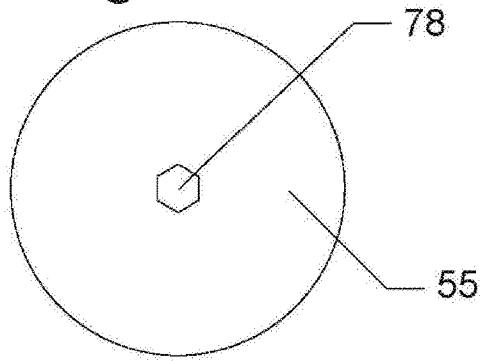
Figure 17F:
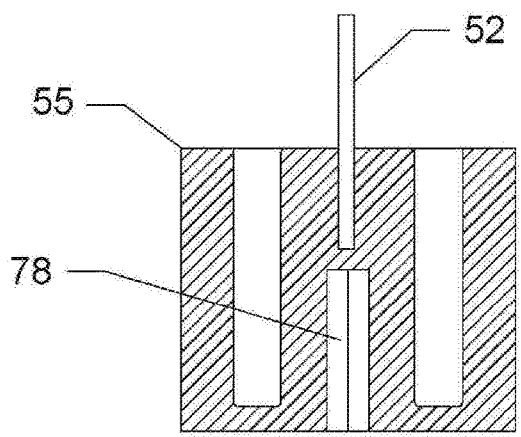
Figure 18A:
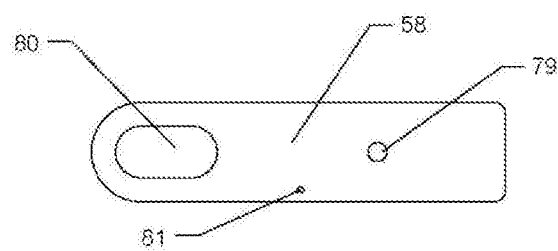
Figure 18B:
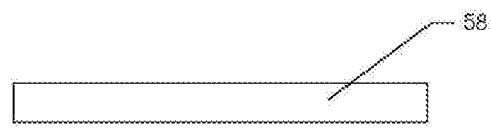
Figure 19A:
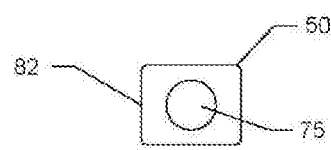
Figure 19B:
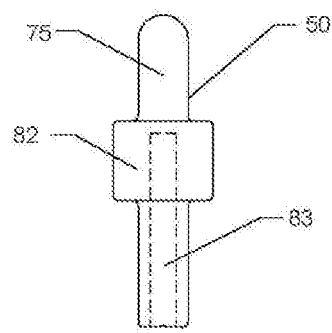
Figure 19C:
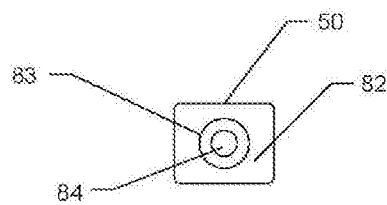
Figure 20A:
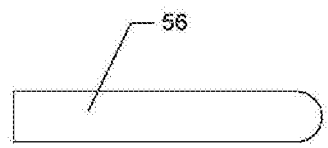
Figure 20B:
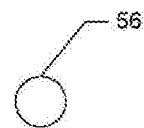
Figure 21A:
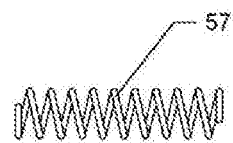
Figure 21B:
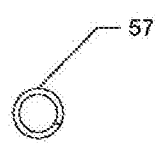
Figure 22A:
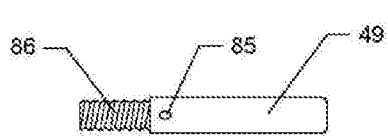
Figure 22B:
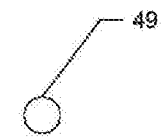
Figure 23A:
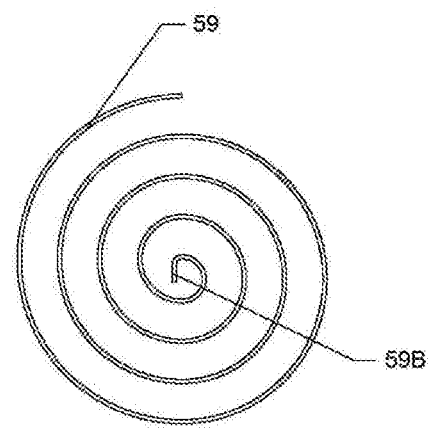
Figure 23B:
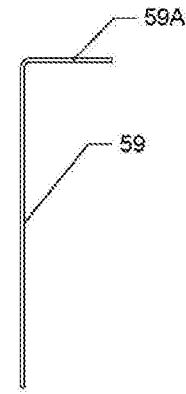
Figure 24A:
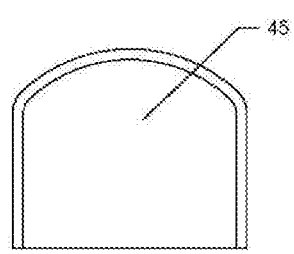
Figure 26A:
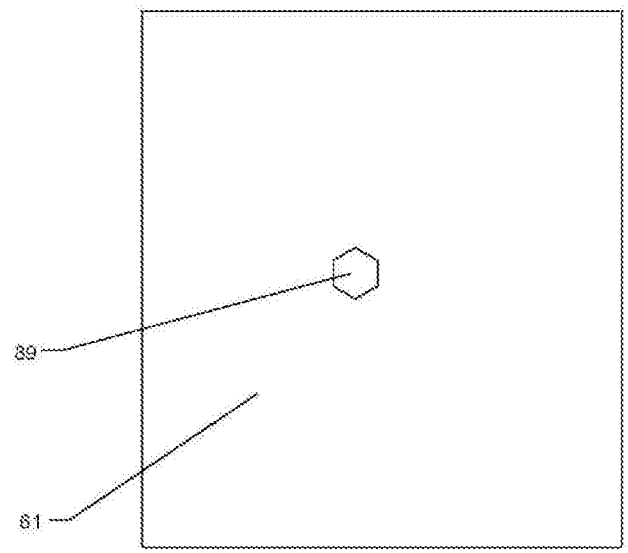
Figure 24B:
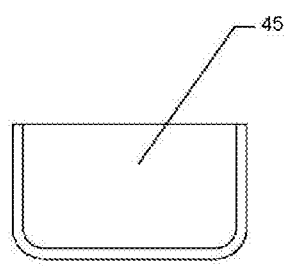
Figure 26B:
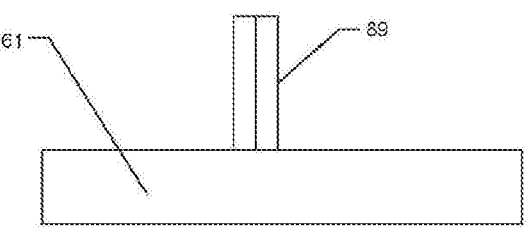
Figure 25A:
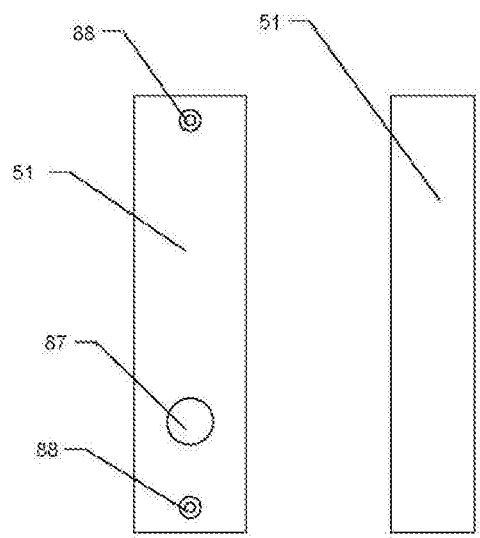
Figure 25B:
Figure 27A:
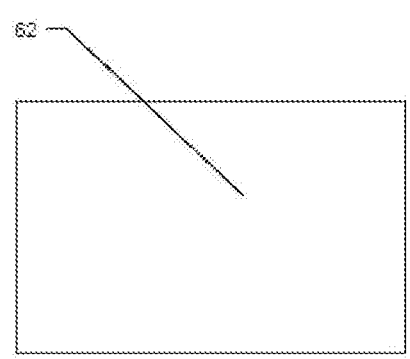
Figure 27B:
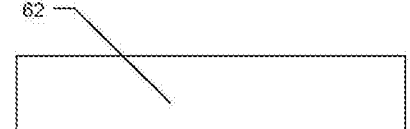
Figure 28A:
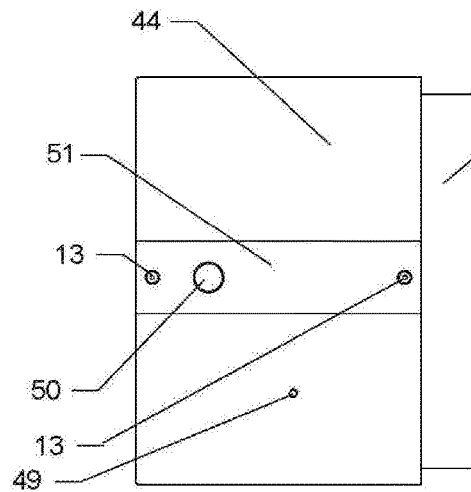
Figure 28B:
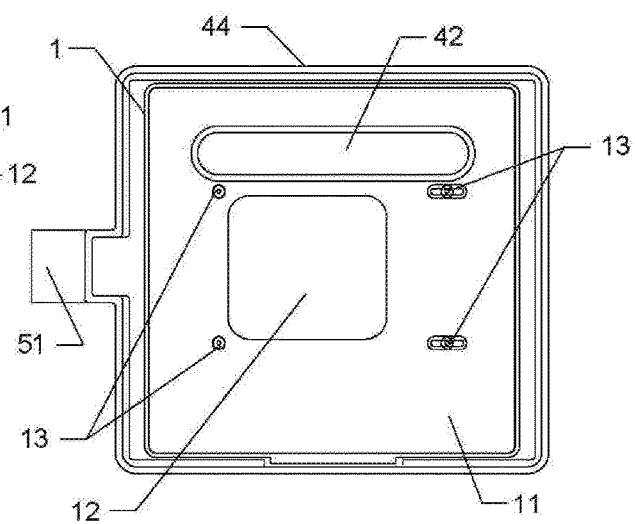
Figure 28C:
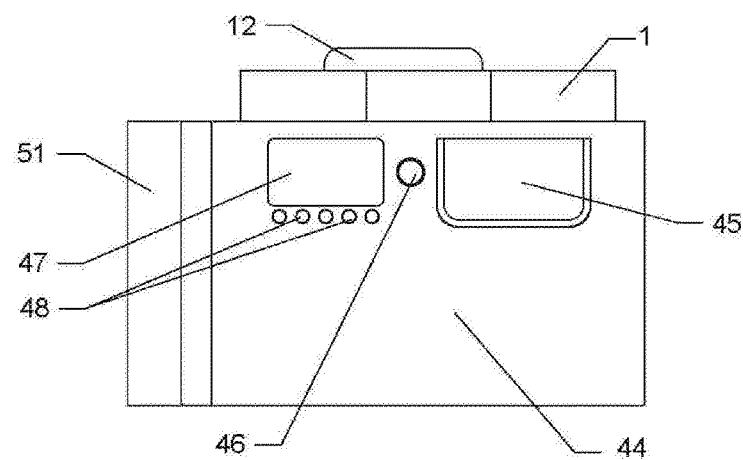

FIG. 15A, FIG. 15B, FIG. 15C and FIG. 15D depict the side, top, front and sectional plan views, respectively, of the housing of the pill dispenser operation box;

FIG. 16A, FIG. 16B and FIG. 16C show the side, top and front plan views, respectively, of the housing cover of the pill dispenser operation box;

FIG. 17A, FIG. 17B, FIG. 17C and FIG. 17F depict the top, front, bottom and sectional plan views, respectively, of a mechanism z-groove barrel-cam of the pill dispenser operation box while FIGS. 17D and 17E show the cut-away detailed portions of the front plan view of the mechanism z-groove barrel cam of the pill dispenser operation box;

FIG. 18A and FIG. 18B show the top and front plan views, respectively, of a mechanism toggle of the pill dispenser operation box:

FIG. 19A, FIG. 19B and FIG. 19C show the top, front and bottom plan views, respectively, of a mechanism follower slide of the pill dispenser operation box:

FIG. 20A and FIG. 20B show the front and side plan views, respectively, of a mechanism follower slide pin of the pill dispenser operation box:

FIG. 21A and FIG. 21B depict the front and side plan views, respectively, of a mechanism follower slide pin spring of the pill dispenser operation box:

FIG. 22A and FIG. 22B show the front and side plan views, respectively, of a mechanism toggle pin of the pill dispenser operation box:

FIG. 23A and FIG. 23B depict the front and side plan views, respectively, of a mechanism spring of the pill dispenser operation box:

FIG. 24A and FIG. 24B show the top and front plan views, respectively, of a pill collector tray of the pill dispenser operation box:

FIG. 25A and FIG. 25B depict the front and side plan views, respectively, of a mechanism locking bar of the pill dispenser operation box;

FIG. 26A and FIG. 26B show the top and front plan views, respectively, of an electric motor and power supply module of the pill dispenser operation box;

FIG. 27A and FIG. 27B depict the top and front plan views, respectively, of the electronics and internet module of the pill dispenser operation box; and FIG. 28A, FIG. 28B and FIG. 28C show the side, top and front plan views, respectively, of installation of the pill dispenser on to the pill dispenser operation box;

The Second Embodiment

Figure 29A:
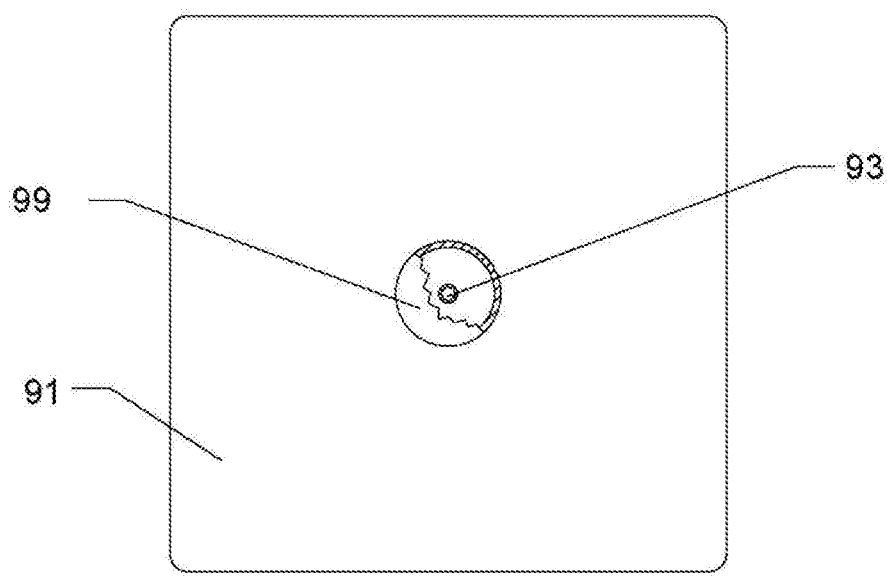
Figure 29B:
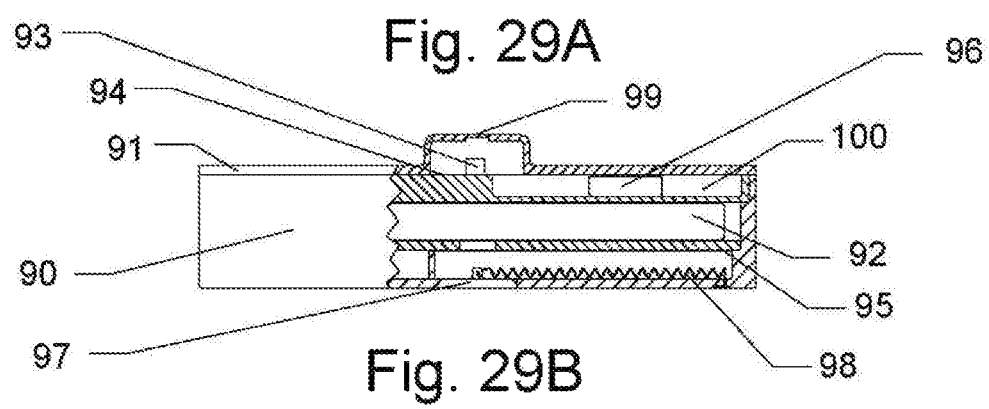
Figure 29C:
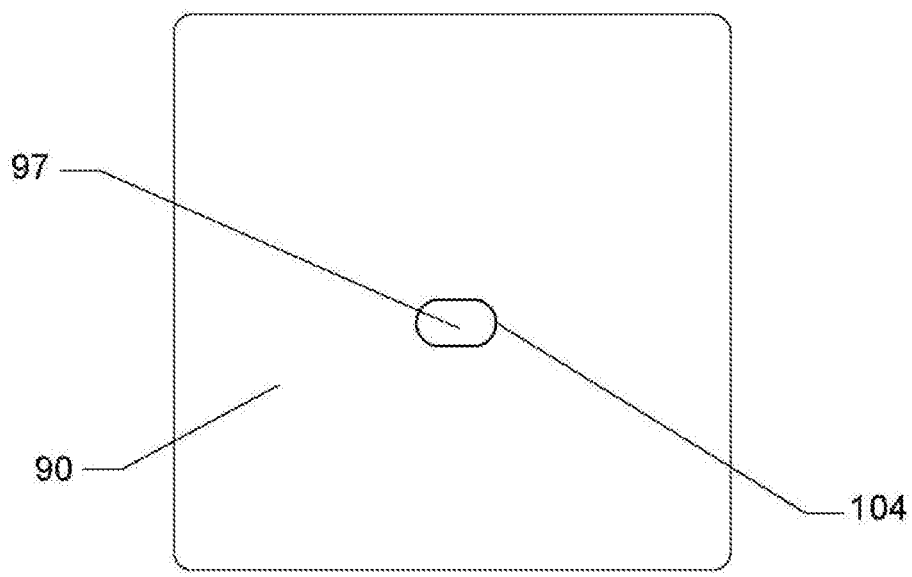
Figure 30A:
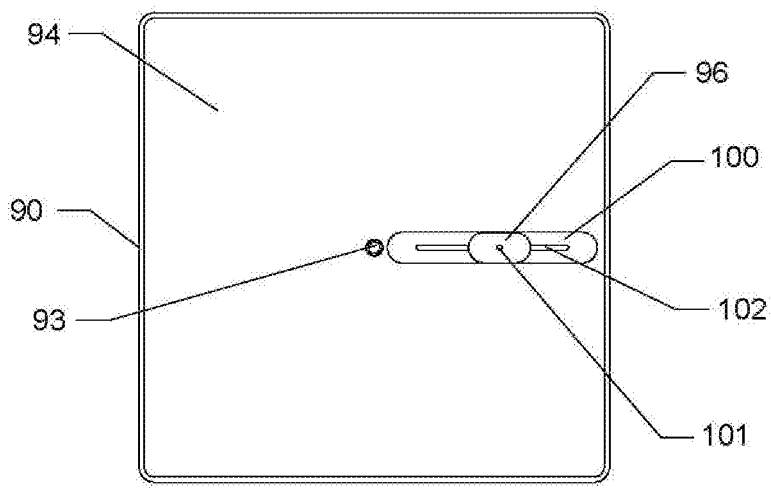
Figure 30B:
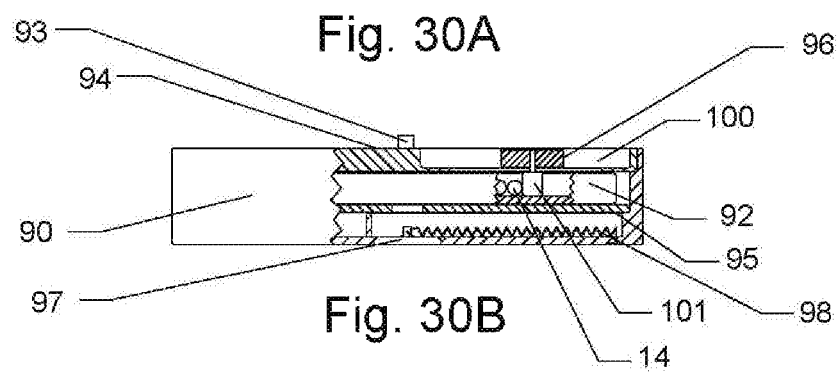
Figure 31A:
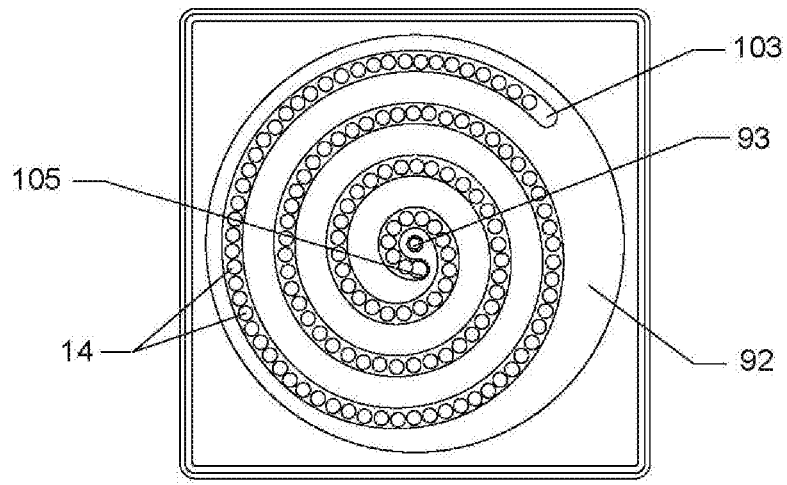
Figure 31B:
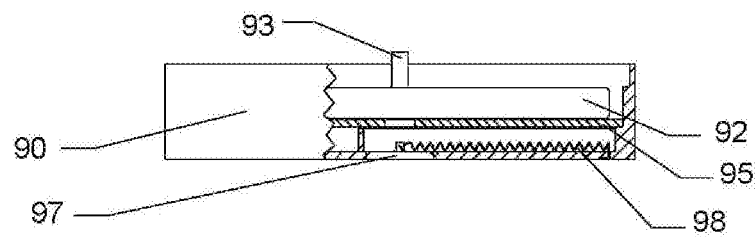

FIG. 29A, FIG. 29B show the top and front plan views with a cut-away respectively, of the pill dispenser using the spiral-groove disk mechanism design, which exhibit some of both exterior and interior parts of the pill dispenser while FIG. 29C shows the bottom plan view of the pill dispenser exhibiting only the exterior parts in accordance with the present invention;

FIG. 30A and FIG. 30B show the top plan view and the front plan view with a cut-away, respectively, of the pill dispenser without the housing cover of the pill dispenser, using the spiral-groove disk mechanism design. These plan views exhibit some of both exterior and interior parts of the pill dispenser; and FIG. 31A and FIG. 31B show the top plan view and the front plan view with a cut-away, respectively, of the pill dispenser without the disk cover of the spiral-groove disk mechanism. These plan views exhibit some of both exterior and interior parts of the pill dispenser:

The Third Embodiment

Figure 32A:
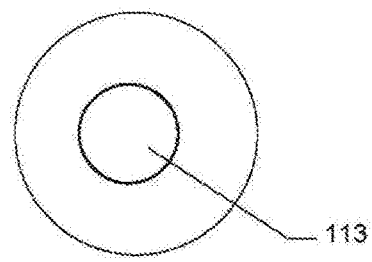
Figure 32B:
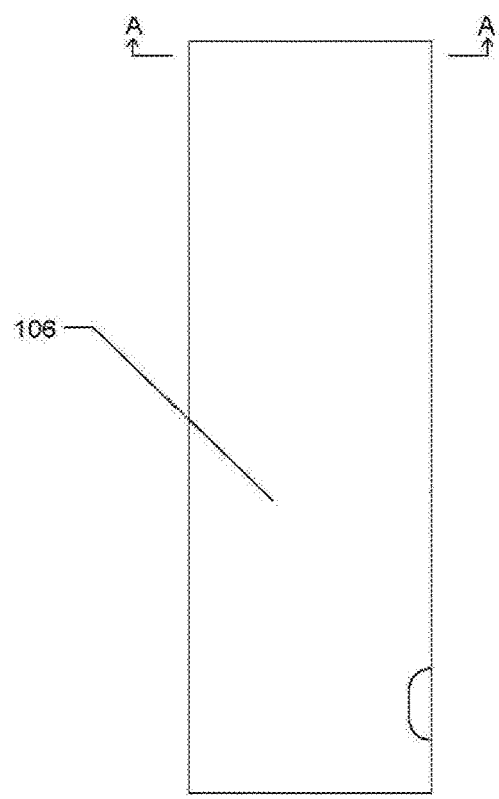
Figure 32C:
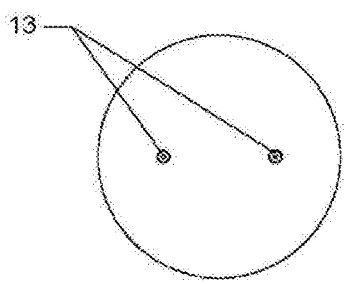
Figure 32D:
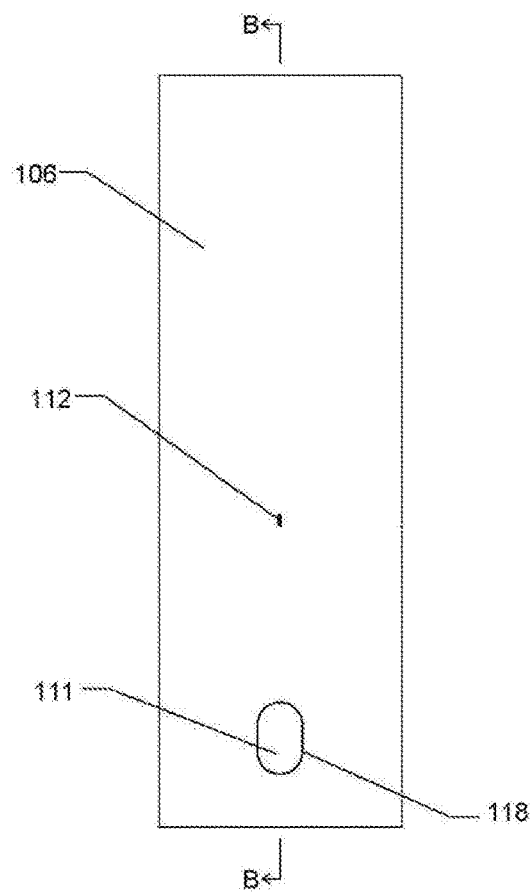
Figure 32E:
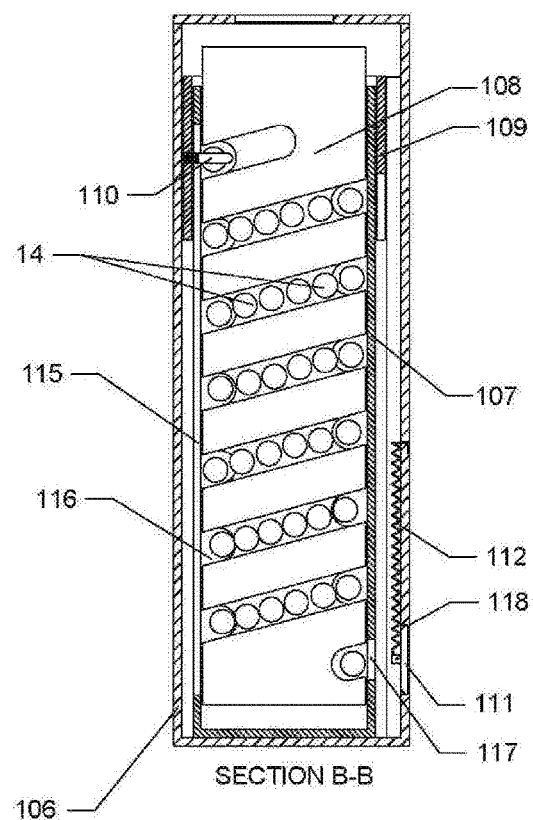
Figure 32F:
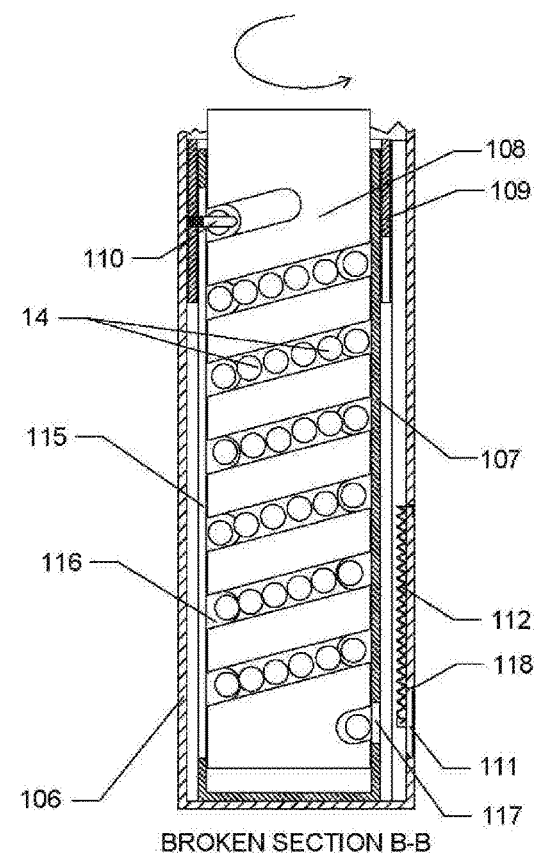
Figure 32G:
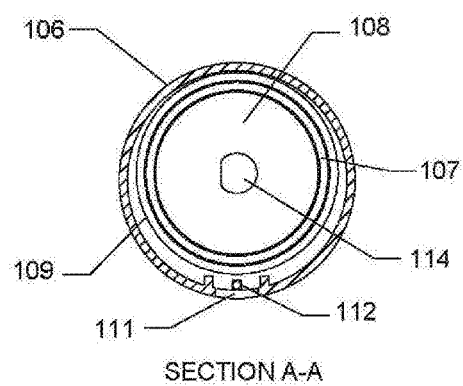

FIG. 32A, FIG. 32B, FIG. 32C and FIG. 32D show the top, front, bottom and side plan views, respectively, of the pill dispenser using the helical-groove cylinder mechanism design, which exhibit only the exterior parts of the pill dispenser in accordance with the present invention; and FIG. 32E, FIG. 32G show the sectional plan views and FIG. 32F shows the broken section view with a cut-away of the pill dispenser using the helical-groove cylinder mechanism design, which exhibit all the interior parts of the pill dispenser in accordance with the present invention.

DETAILED DESCRIPTION OF THE EMBODIMENTS

The First Embodiment

Figure 1A:
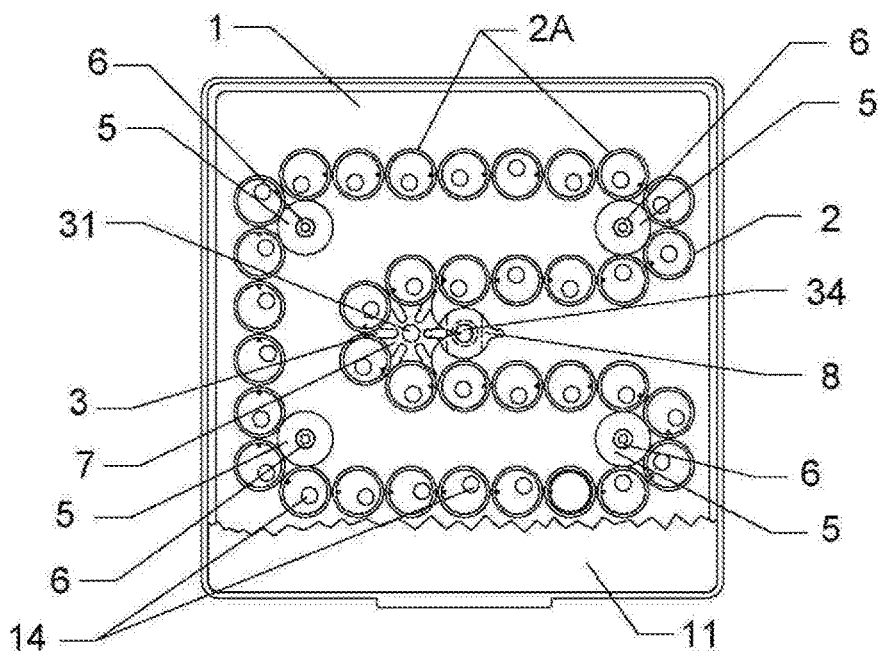
Figure 1B:
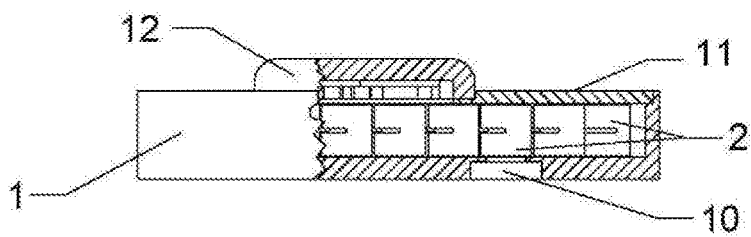
Figure 1C:
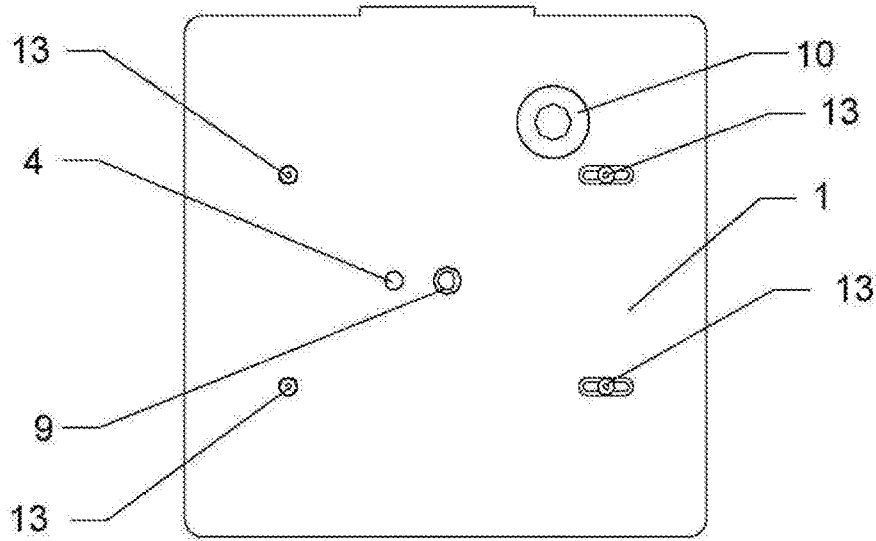
Figure 2A:
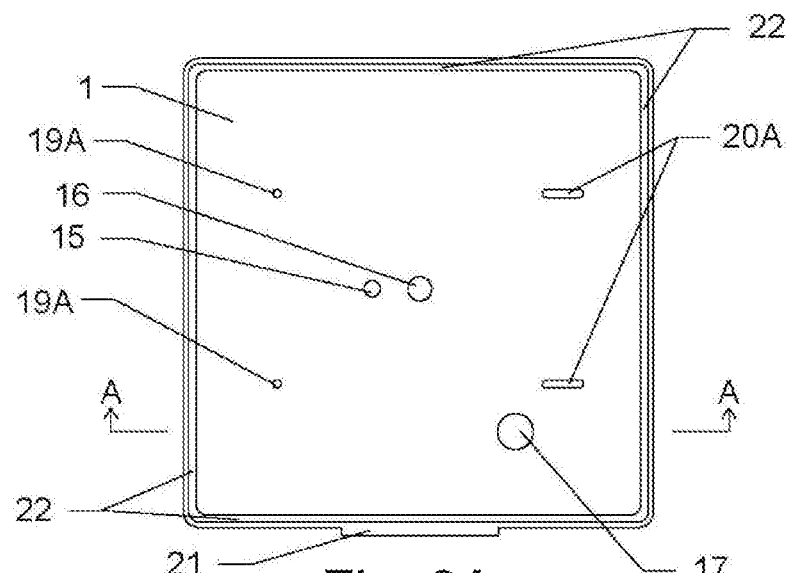
Figure 2B:
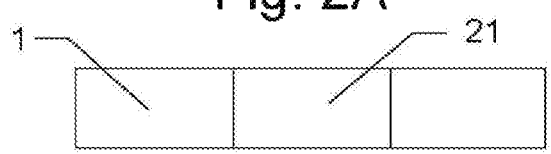
Figure 2C:
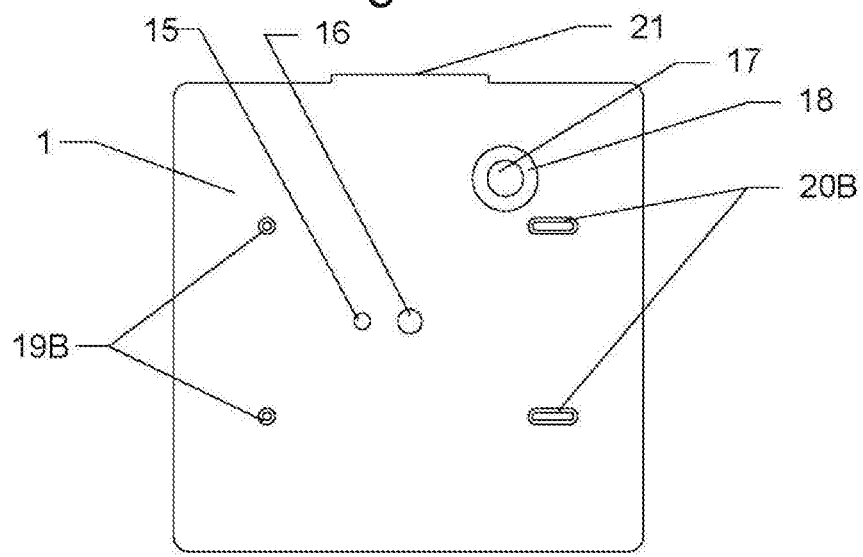
Figure 2D:
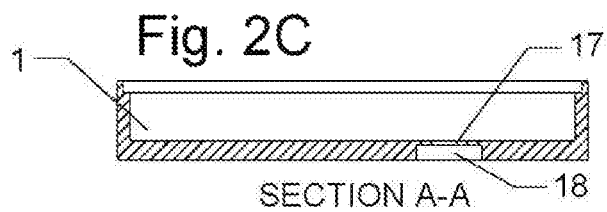
Figure 5A:
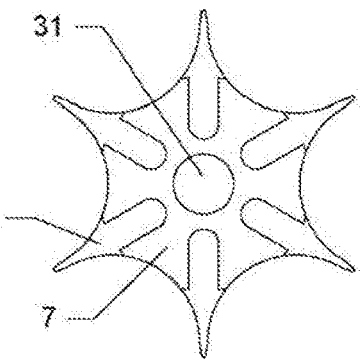
FIG. 5A, FIG. 5B and FIG. 5C show the top, front and bottom plan views, respectively, of the joined sprocket and the Geneva Drive of the pill dispenser using the chain-sprocket and Geneva-mechanism design.
Figure 5B:
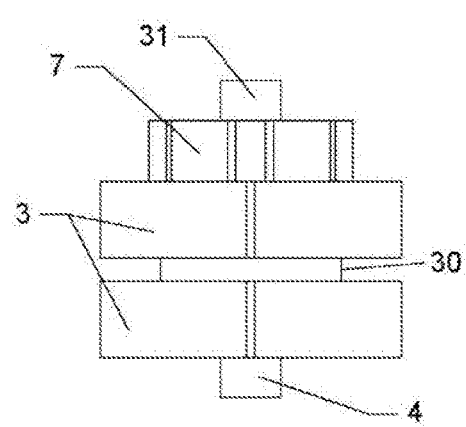
Figure 6A:
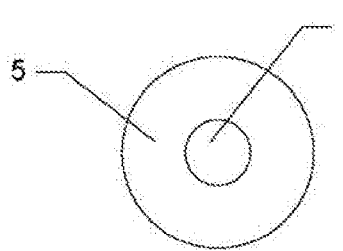
FIG. 6A and FIG. 6B depict the top and front plan views, respectively, of the idler roller of the pill dispenser using the chain-sprocket and Geneva-mechanism design.
Figure 7A:
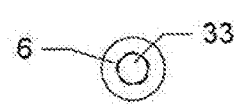
FIG. 7A and FIG. 7B show the top and front plan views, respectively, of the stud of the pill dispenser using the chain-sprocket and Geneva-mechanism design.
Figure 6B:
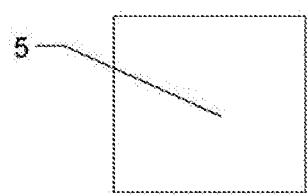
Figure 7B:
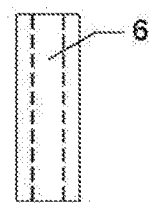
Figure 5C:
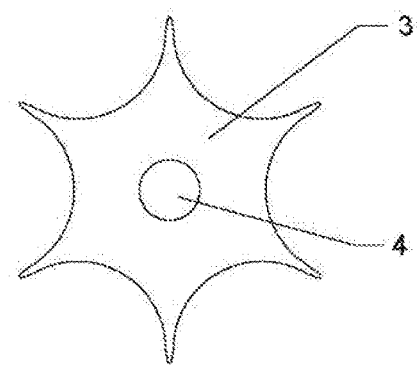
Figure 8A:
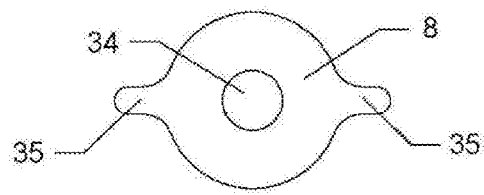
FIG. 8A, FIG. 8B and FIG. 8C depict the top, front and bottom plan views, respectively, of the Geneva driver of the pill dispenser using the chain-sprocket and Geneva-mechanism design.
Figure 8B:
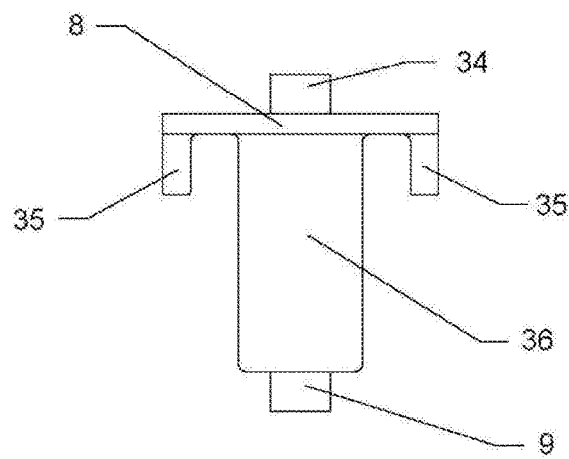
Figure 8C:
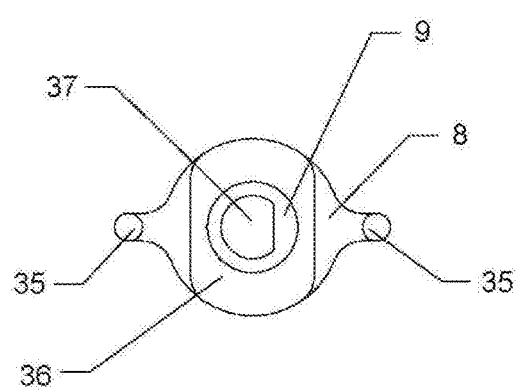
Figure 11A:
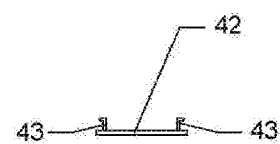
FIG. 11A, FIG. 11B and FIG. 11C show the front, bottom and side plan views, respectively, of the pill fill access cover of the pill dispenser using the chain-sprocket and Geneva-mechanism design.

Now, referring to FIG. 1A, FIG. 1B and FIG. 1C which are top, front and bottom plan views, respectively of a first embodiment of the pill dispenser in accordance with the present invention, and to FIG. 2A which is a top plan view of a pill dispenser housing 1, and include a sprocket 3 and a Geneva drive 7 which is affixed or integral to the sprocket 3 that is installed into a hole 15 of the pill dispenser housing 1 via an integral bottom sprocket spindle 4 whose top, front and bottom plan views are more clearly shown in FIG. 5A, FIG. 5B and FIG. 5C, respectively. To engage with the Geneva drive 7, a Geneva driver 8 is installed into a hole 16 of the pill dispenser housing 1 via an integral Geneva driver bottom spindle 9 whose top, front and bottom plan views are more clearly shown in FIG. 8A, FIG. 8B and FIG. 8C, respectively. During a rotary motion of the Geneva driver 8, a crank 35 of the Geneva driver 8 engages repeatedly with the Geneva drive 7 while allowing to continue an intermittent rotation of the Geneva drive 7 without any interference due to a truncated base 36 of the Geneva driver 8.

A plurality of idler rollers 5 is installed on to a stud 6 which is pre-installed into a hole 19A of the pill dispenser housing 1 via a screw 13 which goes into a thru threaded hole 33 of the stud 6. The head of screws 13 is flush with the bottom flat surface of the pill dispenser housing 1 with a provision of counter bores 19B at the bottom flat surface of the pill dispenser housing 1.

Figure 1D:
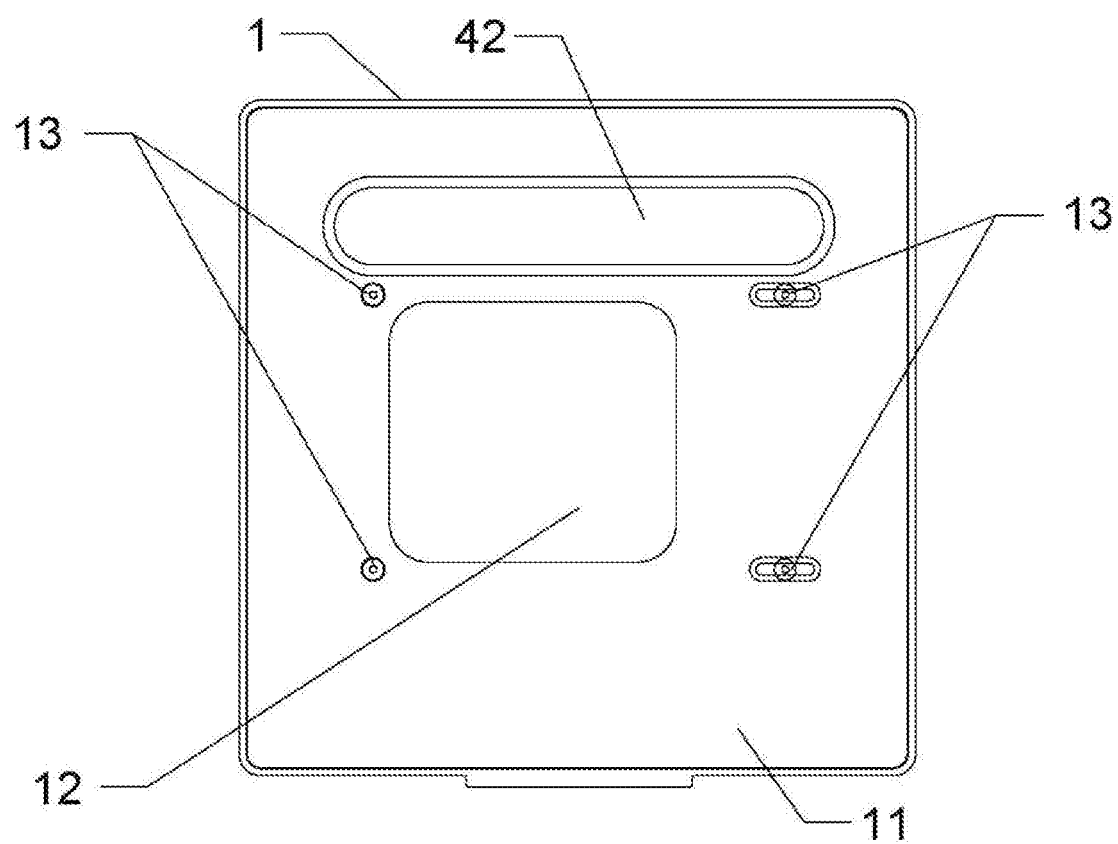
Figure 1E:
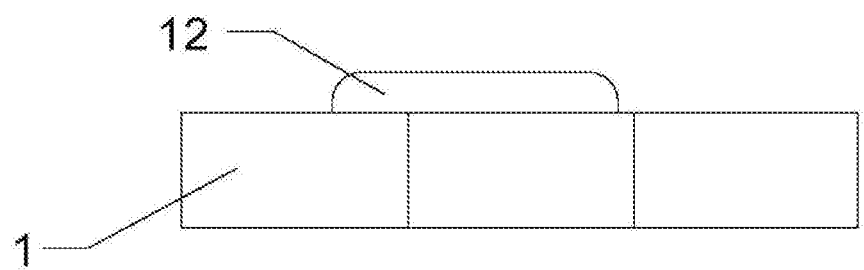
Figure 1F:
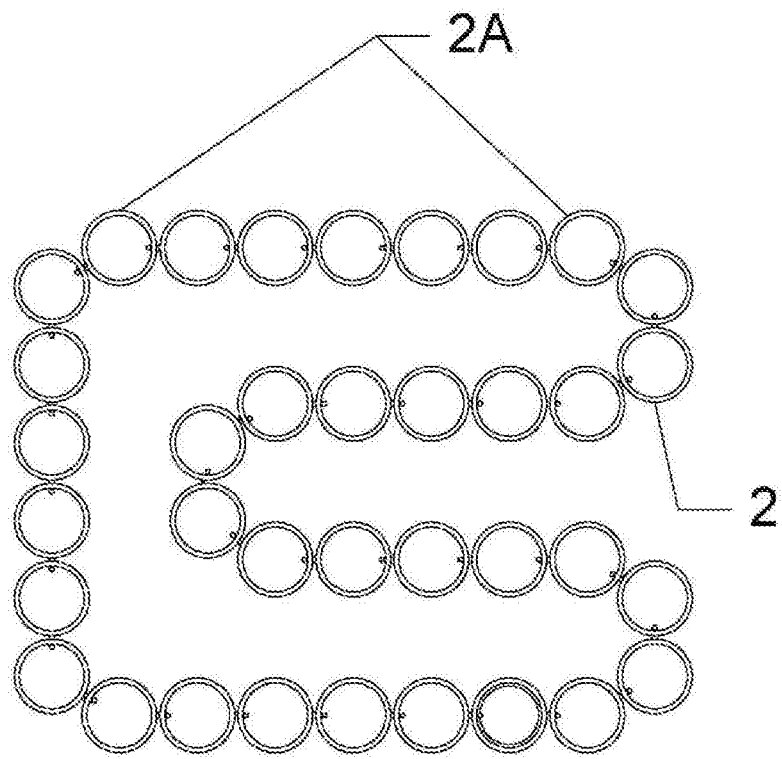
Figure 1G:
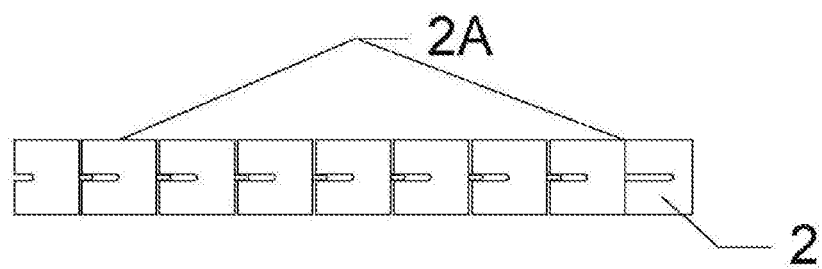
Figure 4A:
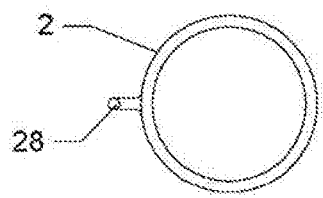
FIG. 4A, FIG. 4B and FIG. 4C depict the top, front and side plan views, respectively, of the pill ring of the pill dispenser using the chain-sprocket and Geneva-mechanism design.
Figure 4B:
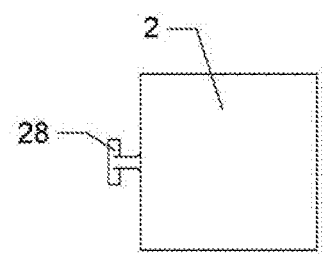
Figure 4C:
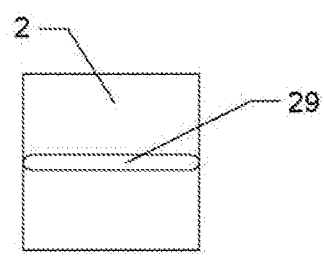

Referring to FIG. 1F and FIG. 1G which are top and front plan views, respectively, of a pill ring chain 2A, and to FIG. 4A, FIG. 4B and FIG. 4C which are top, front and side plan views, respectively, of a pill ring 2, and include a plurality of pill rings 2 which are linked together via a hook 28 on one side of the pill ring 2 and an open slot 29 on the opposite side of the pill ring 2, thereby forming the pill ring chain 2A in a closed loop fashion.

Figure 9A:
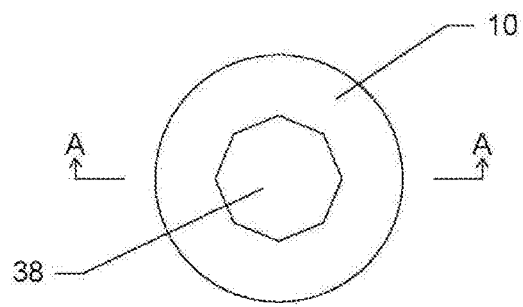
FIG. 9A and FIG. 9B show the top and mid sectional plan views, respectively, of the pill plug of the pill dispenser using the chain-sprocket and Geneva-mechanism design.
Figure 9B:
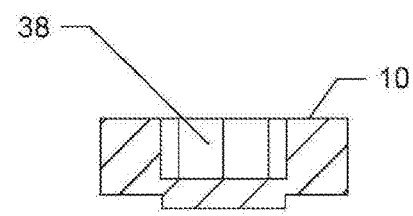

As clearly shown in FIG. 1A, FIG. 1B and FIG. 1C, the pill ring chain 2A is placed in the pill dispenser housing by making a belt-like contact to the idler rollers 5 and by engaging with the sprocket 3 like a chain-and-sprocket mechanism. A pill plug 10 is temporarily installed via a breakable adhesive (not shown) into a counter bore 18 of a pill exit hole 17 of the pill dispenser housing 1 with a tool (not shown) that matches the recessed shape 38 of the pill plug 10 whose top and transverse mid sectional plan views are more clearly shown in FIG. 9A and FIG. 9B, respectively.

As shown, in FIG. 1A, pills 14, single or multiple, packaged, unpackaged, individually-package or multiply-packaged, are dropped into each pill ring 2 one by one per the prescribed dosage while translationally moving the pill ring chain 2A.

Figure 3A:
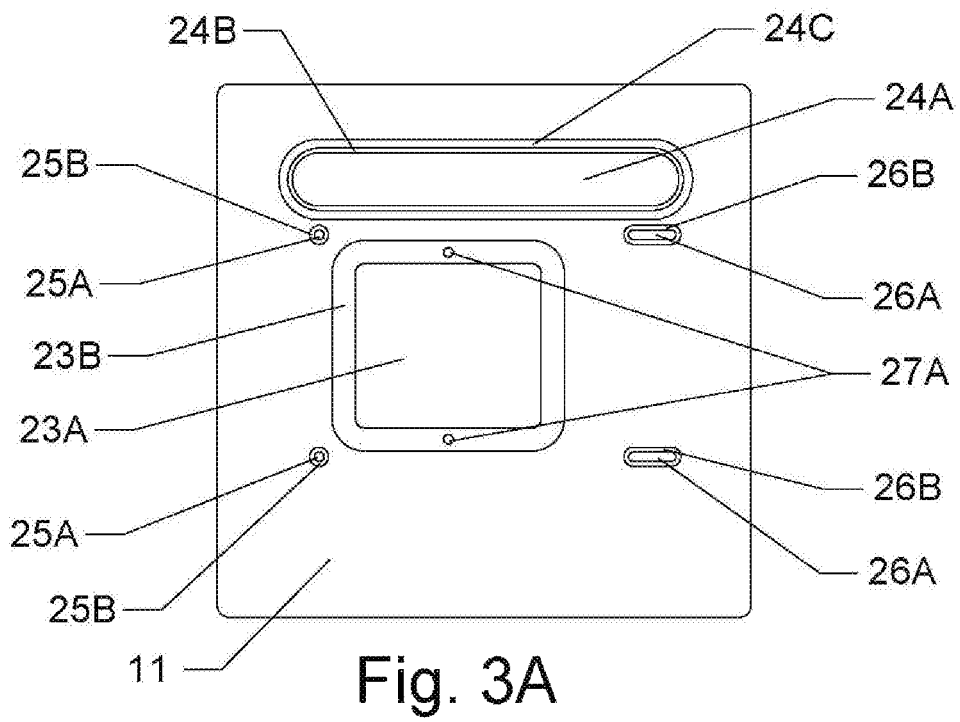
FIG. 3A, FIG. 3B and FIG. 3C show the top, front and bottom plan views, respectively, of the housing cover of the pill dispenser using the chain-sprocket and Geneva-mechanism design.
Figure 3B:
Figure 3C:
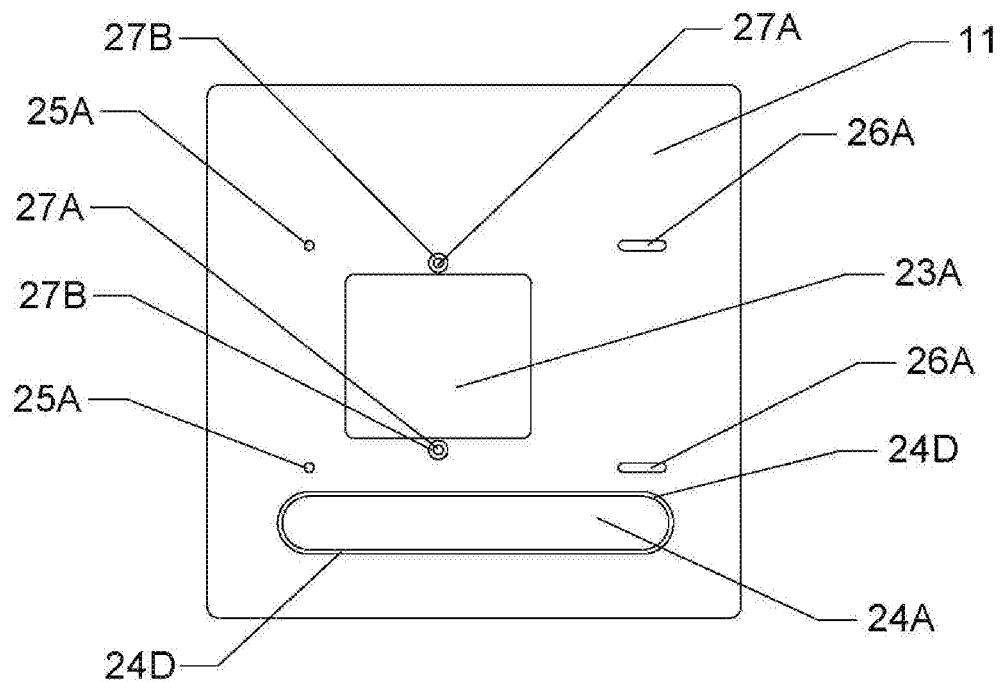
Figure 10A:
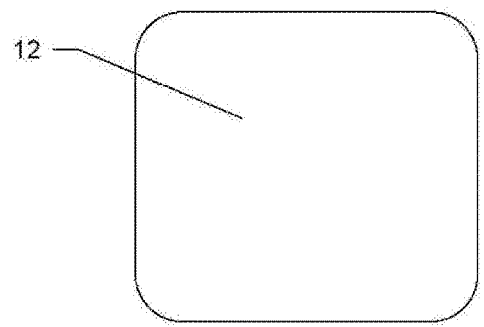
FIG. 10A, FIG. 10B and FIG. 10C depict the top, sectional and bottom plan views, respectively, of the sprocket-Geneva mechanism cap of the pill dispenser using the chain-sprocket and Geneva-mechanism design.
Figure 10B:
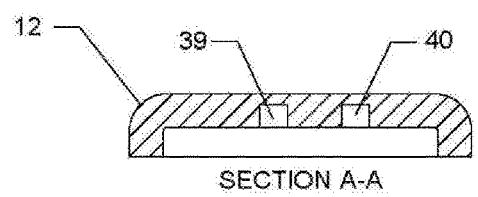
Figure 10C:
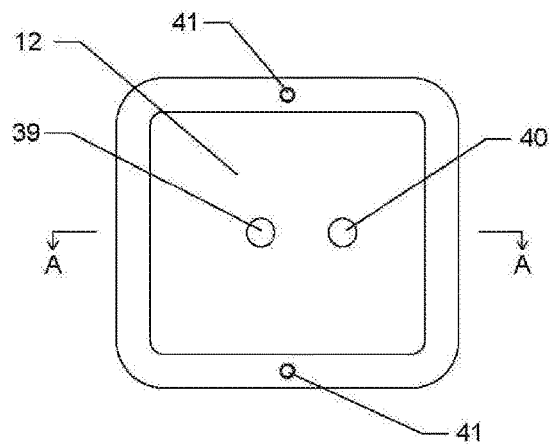
Figure 11B:
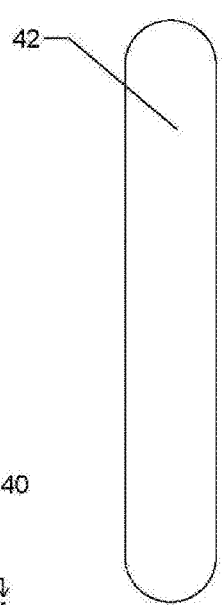
Figure 11C:
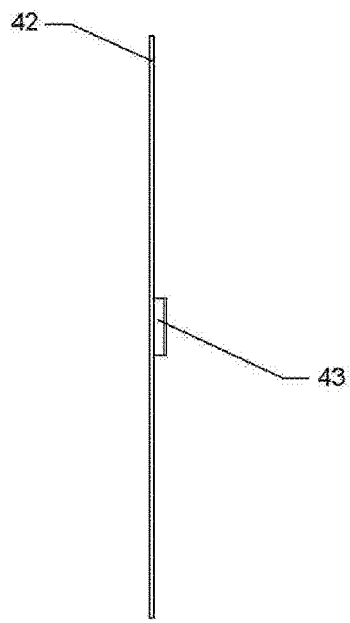

Referring to FIG. 3A and FIG. 3C which are top and bottom plan views, respectively. of a pill dispenser housing cover 11, and to FIG. 10C which is a bottom plan view of a sprocket-Geneva mechanism cap 12, affixed is the sprocket-Geneva mechanism cap 12 to the flat surface of the pill dispenser housing cover 11 via screws (not shown), as an example of one of many other fastening methods which are commercially available and can be used instead of the screws (not shown), at the locations of holes 27A of the pill dispenser housing cover 11 while the holes 27A are aligned with holes 41 of the sprocket-Geneva mechanism cap 12. The head of screws (not shown) is flush with the other or bottom flat surface of the pill dispenser cover 11 with a provision of counter bores 27B at the bottom flat surface of the pill dispenser housing cover 11.

As depicted in FIG. 1D and FIG. 1E, and referring to FIG. 2A, FIG. 3A, FIG. 10B, FIG. 10C, FIG. 11A, FIG. 11B and FIG. 11C, the pill dispenser housing cover 11 with the sprocket-Geneva mechanism cap 12. Is mounted on an internally surrounded wall ledge 22 of the pill dispenser housing while aligning a blind hole 39 of the cap 12 with an integral top sprocket spindle 31 of the sprocket 3 and also aligning with another blind hole 40 of the cap 12 with an integral Geneva driver top spindle 34 of the Geneva driver 8, and also aligning holes 25A and slots 26A of the pill dispenser housing cover 11 and securing the pill dispenser housing cover 11 via the screws 13 installed into the thru threaded hole 33 of the stud 6. The head of screws 13 is flush with the top flat surface of the pill dispenser housing cover 11 with a provision of counter bores 25B and counter-bore slots 26B at the top flat surface of the pill dispenser housing cover 11. The pill ring chain 2A filled with the pills 14 is checked through a fill access slot 24A of the pill dispenser housing cover 11 while translationally moving the pill ring chain 2A with a human finger. Now, a fill access cover 42 is installed onto the counter-bore slot 24B of the pill dispenser housing cover 11 while allowing snaps 43 of the fill access cover to engage with a top ridge surface 24C and a bottom ridge surface 24D of the fill access slot 24A.

Figures 15A, 15B:
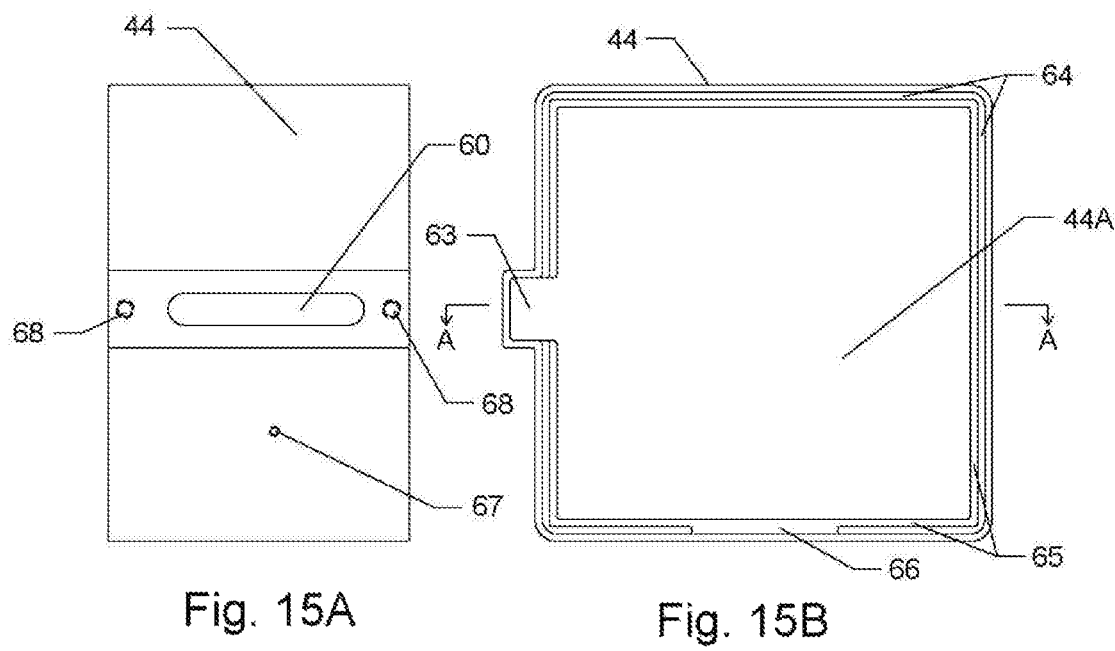
Figure 15C:
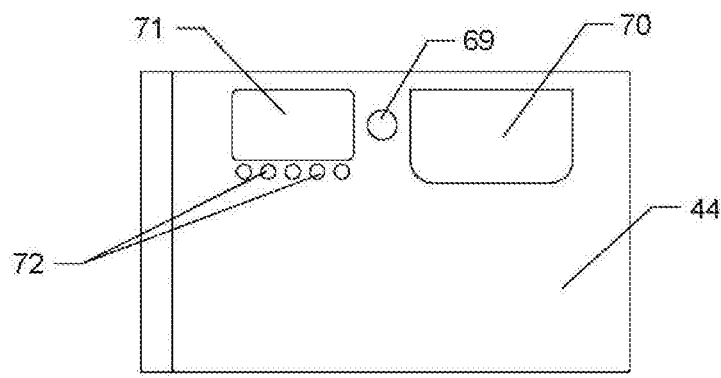
Figure 15D:
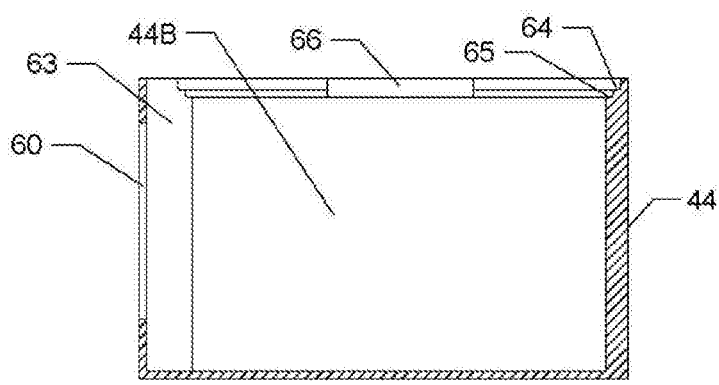

For the operation of the pill dispenser, now, referring to FIG. 12A, FIG. 12B and FIG. 12C which are side, top and front plan views, respectively, and FIG. 13A, FIG. 13B, FIG. 13C, and FIG. 13D which are side and top plan views with a cut-away and front and side transverse sectional plan views of an embodiment of the pill dispenser operation box with an electrical operation and a backup manual operation mechanism in accordance with the present invention, and further referring to FIG. 15A, FIG. 15B, FIG. 15C which are side, top and front plan views, respectively, of a pill dispenser operation box housing 44, and include an electric motor and power supply module 61 whose top and front plan views are more clearly shown in FIG. 26A and FIG. 26B, respectively, and an electronics and internet module 62 whose top and front plan views are more clearly shown in FIG. 27A and FIG. 27B, respectively. The electric motor and power supply module 61 is affixed to an interior wall surface 44A of the pill dispenser operation box housing 44 via a fastener (not shown), and the electronics and internet module 62 is affixed to an interior wall surface 44B of the pill dispenser operation box housing 44 via a fastener (not shown).

For a user images and interface, a camera 46 (not shown in full details) and a display 47 (not show in full details) and 48 light-emitting diodes (not shown in full details) are connected to the electronics and internet module 62 and are installed on openings 69, 71 and 72, respectively of the pill dispenser operation box housing 44. For accessing and retrieving pills, a pill collector tray 45 whose top and front plan views are more clearly shown in FIG. 24A and FIG. 24B, respectively is installed into an opening 70 of the pill dispenser operation box housing 44.

For the backup manual operation of the pill dispenser operation box, a mechanism toggle pin 49 whose top and side plan views are more clearly shown in FIG. 22A and FIG. 22B, respectively, is installed via a threaded end 86 of the mechanism toggle pin into a threaded hole 67 of the pill dispenser operation box housing 44. A mechanism follower slide pin 56 whose front and side plan views are more clearly shown in FIG. 20A and FIG. 20B, respectively, together with a mechanism follower slide pin spring 57 whose front and side plan views are more clearly shown in FIG. 21A and FIG. 21B, respectively is installed into a longitudinal blind hole 84 of a shaft 83 of a mechanism follower slide 50 whose top, front and bottom plan views are more clearly shown in FIG. 19A, FIG. 19B and FIG. 22C, respectively. A mechanism toggle 58 whose top and front plan views are more clearly shown in FIG. 18A and FIG. 18B, respectively, is installed on to the shaft 83 of the mechanism follower slide 50 via a pivoting slot 80 of the mechanism toggle 58. A mechanism toggle spring 59 whose front and side plan views are more clearly shown in FIG. 19A and FIG. 19B, respectively, is attached via an outer bent end 59A of the mechanism toggle spring 59 into a hole 79 of the mechanism toggle 58.

The mechanism follower slide 50 with the mechanism follower slide pin spring 57, the mechanism follower slide pin 56, the mechanism toggle 58, and the mechanism toggle spring 59 is installed into a slot 60 of the pill dispenser operation box housing 44 while a sliding portion 82 of the mechanism follower slide resides in an adjacent slot 63 of the pill dispenser operation box housing 44. For its pivoting and retracting, the mechanism toggle 58 is installed on to the toggle pin 49 via a pivot hole 79 of the mechanism toggle 58 while the inner bent end 59B of the attached mechanism toggle spring 59 is installed into the cross hole 85 of the mechanism follower slide pin 56.

A mechanism Z-groove barrel cam 55, whose top, front, bottom, transverse mid sectional, and z-groove's straight and inclined cut-away sectional plan views are more clearly shown in FIG. 17A, FIG. 17B, FIG. 17C, FIG. 17D, FIG. 17E and FIG. 17F, respectively, is installed on to an electric motor shaft 89 of the electric motor and power supply module 61 via a blind coupling hole 78 of the mechanism Z-groove barrel cam 55 while the mechanism follower slide pin 56 is in contact with the mechanism Z-groove barrel cam but not yet allowed inside the groove 77 of the mechanism Z-groove barrel cam 55 with an aid of a mechanism locking bar 51 whose front and side plan views are more clearly shown in FIG. 25A and FIG. 25B, respectively, by having a tip 75 of the mechanism follower slide 50 temporarily reside in a hole 87 of the mechanism locking bar 51 which is detachable when a need arise to manually operate the pill dispenser operation box. The mechanism locking bar 51 is detachably attached to the pill dispenser operation box housing 44 via screws 13 through the counter-bore holes 88 of the locking mechanism bar 51 to threaded holes 68 of the pill dispenser operation box housing 44.

To enclose the top of the pill dispenser operation box, a pill dispenser operation box housing cover 53 whose side, top and front plan views are more clearly shown in FIG. 16A, FIG. 16B and FIG. 16C, respectively is affixed via fasteners (not shown) to an internally surrounded wall ledge 65 of the pill dispenser operation box housing while having an integral pill dispenser coupling spindle 52 of the mechanism Z-groove barrel cam 55 pass through a hole 53 of the pill dispenser operation box housing cover 53 and also covering the adjacent slot 63 and encompassing the rectangular notch 66 of the pill dispenser operation box housing 44 with tabs 73 and 74, respectively of the pill dispenser operation box housing cover 53.

As clearly shown in FIG. 14A, FIG. 14B, FIG. 14C, and FIG. 14D which are a side plan view, a top plan view with a cut-away, a side transverse sectional plan view and an enlarged cut-away detail view of the pill dispenser operation box in a backup manual operation mode for which the mechanism locking bar 51 is detached and the mechanism follower slide 50 is lifted to allow to engage the mechanism follower slide pin 56 with the groove 77 of the mechanism Z-groove barrel cam 55. During the manual operation, the mechanism provides a discrete rotary motion while sliding up and down repeatedly the tip 75 of the mechanism follower slide 50.

The pill dispenser that is filled with the pills 14 and that is ready to be used is inserted into the pill dispenser operation box as depicted in FIG. 28A, FIG. 28B, FIG. 28CIG. 14D which are a side, top and front plan views, respectively of the pill dispenser and the pill dispenser operation box together. During the insertion process, the pill plug 10 of the pill dispenser is removed with a special tool (not shown), the pill exit hole 17 of the pill dispenser is aligned with a hole 54 of the pill dispenser operation box housing cover 53 via matching the rectangular notch 66 of the pill dispenser operation box housing 44 with a key rib 21 of the pill dispenser housing 1, the integral pill dispenser coupling spindle 52 of the mechanism Z-groove barrel cam 55 is coupled with the an integral Geneva driver bottom spindle 9 via a coupling hole 37 of the Geneva driver 8.

The Second Embodiment

Referring to FIG. 29A, FIG. 29B and FIG. 29C which are top, front plan views with a cut-away to show inner parts and a bottom plan view, respectively of a second embodiment of the pill dispenser and also for more details, referring to FIG. 30A and FIG. 31A which are top plan views and FIG. 30B and FIG. 31B which are front plan views with a cut-away to show the inner parts of the second embodiment of the pill dispenser in accordance with the present invention, and include a spiral groove disk 92 with a freely-rotating integral disk spindle 93 which is install on to a platform 95 which is in turn detachably attached to a housing 90 enclosing the spiral groove disk 92 and a disk cover 94. The housing 90 is closed by a housing cover 91 which has a cap 99.

Below the platform 95, the housing 90 has an internally mounted detachable pill plug 97 to which attached is a plug spring 98 which in turn is attached to the housing 90. The pill plug 97 is detached externally with a special tool (not shown) and retracted due to a restoring force of the pill plug spring 98.

A partially blind slot 100 on the disk cover 94 is used by a slide 96 in which mounted is a pill pin 101. A narrow slot 102 within and along the partially blind slot 100 is used by the pill pin 101 for traveling along with the slide 96. The pill pin 101 engages with the groove 103 of the spiral groove disk 92 and moves inside the groove 103 while pushing pills 14 residing in contact with one another within the groove 103 during the rotary motion of the spiral groove disk 92 which rotary motion is caused by rotating the integral disk spindle 93.

After the pill plug 97 is removed, the push of the pill pin 101 forces the pills to exit through an exit hole 105 one at a time while being dispensed from a hole 104 of the detachable pill plug 97.

For its electrical operation, the disk spindle 93 of the spiral-groove disk pill dispenser, as a second embodiment, can be coupled, while breaking the cap 99, to a pill dispenser operation box which is similar to the pill dispenser operation box of the first embodiment described in detail above.

The Third Embodiment

Referring to FIG. 32A, FIG. 32B, FIG. 32C and FIG. 32D which are top, front, bottom and side plan views, respectively of a third embodiment of the pill dispenser and also for more details, referring to FIG. 32 E, FIG. 32F and FIG. 32G which are transverse front sectional, broken front sectional and top sectional plan views, respectively, to show the inner parts of the third embodiment of the pill dispenser in accordance with the present invention, and include a helical groove cylinder 108 with a blind coupling hole 114 for rotating the helical groove cylinder 108 which resides in a slip-fit sleeve 107 which in turn is eccentrically affixed via screws 13 to a housing 106 enclosing the helical groove cylinder 108 and a tubular slide 109. The housing 106 is closed by an integral thin disk 113 which is breakable.

The sleeve 107 has an open longitudinal slot 115 which is used for traveling by the tubular slide 109 via a pill pin 110 which in turn is affixed to the tubular slide 109. The pill pin 110 engages with the groove 116 of the helical groove cylinder 108 and moves inside the groove 116 while pushing pills 14 residing in contact with one another within the groove 116 during the rotary motion of the helical groove cylinder 108 which rotary motion is caused by an externally rotating shaft (not shown) coupled with helical groove cylinder 108 via the blind coupling hole 114.

Below the sleeve 107, the housing 106 has an internally mounted detachable pill plug 111 to which attached is a plug spring 112 which in turn is attached to the housing 106. The pill plug 111 is detached externally with a special tool (not shown) and retracted due to a restoring force of the pill plug spring 112

After the pill plug 112 is removed, the push of the pill pin 110 forces the pills to exit through an exit hole 117 one at a time then being dispensed from a hole 118 of the detachable pill plug 111.

For its electrical operation, the coupling hole 114 of the helical-groove cylinder pill dispenser, as a third embodiment, can be coupled, while breaking the thin disk 113, to a pill dispenser operation box which is similar to the pill dispenser operation box of the first embodiment described in detail above.

The invention claimed is:

1. A tamper-resistant pill and/or capsule dispenser for attachment to an electronic control and communication unit including inter alia, an electric actuator mechanism, a microprocessor, a graphical user interface and a communications unit, the dispenser including sensors operative under control of said electronic control and communication unit to monitor and dispense prescribed dosages of medications or vitamin supplements in pill and/or capsule form and help control, track and maintain a record of pills and/or capsules dispensed to a patient to ensure that the dispensed product is not improperly removed from or replaced in the dispenser, said dispenser comprising:

a housing having an open top, and a generally closed bottom except for a pill dispensing opening formed therein.

a spindle mounted, generally circular disk disposed within said housing, said disk having a spiral groove formed in a first surface thereof facing said open top, said groove extending from a point proximate the outer perimeter of said disk to a first pill exiting aperture formed in said disk proximate the spindle carrying said disk, said groove being adapted to slidably carry pills and/or capsules to be sequentially dropped through said first pill exiting aperture; and a housing closure plate having a central opening formed therein through which said spindle extends for driving engagement with the actuator mechanism of the electronic control and communication unit, said closure plate further having a radially extending slot formed in the outer surface of said closure plate for carrying a slider connected via a narrow slit formed in the base of said slot to a pill pin adapted to extend into said spiral groove for engaging pills residing in said groove and advancing them along said groove toward said first pill exiting aperture as said disk is rotated by said actuator mechanism, whereby pills dropping through said first pill exiting aperture are dispensed through said dispensing opening.

2. A tamper-resistant pill and/or capsule dispenser for attachment to an electronic control and communication unit including inter alia, an electric actuator mechanism, a microprocessor, a graphical user interface and a communications unit, the dispenser including sensors operative under control of said electronic control and communication unit to monitor and dispense prescribed dosages of medications or vitamin supplements in pill and/or capsule form and help control, track and maintain a record of pills and/or capsules dispensed to a patient to ensure that the dispensed product is not improperly removed from or replaced in the dispenser, said dispenser comprising:

a generally cylindrical housing having an open top, and a generally closed bottom, except for a pill dispensing opening formed in a lower side portion of the cylindrical housing;

a cylindrical sleeve open at its top end and closed at its bottom end, said sleeve being eccentrically disposed within said cylindrical housing and away from the side of said cylindrical housing having said pill dispensing opening, said sleeve being affixed at its bottom end to the bottom end of said cylindrical housing and having an open, longitudinally extending slot formed in the side thereof opposite said pill dispensing opening;

an axially rotatable cylinder disposed within said housing, said cylinder having a helical indented groove formed in the outer cylindrical surface thereof, said groove extending from a point proximate an upper end of said cylinder to a point proximate a lower end of said cylinder, said groove being adapted to slidably carry pills and/or capsules to be sequentially passed through a first pill exiting aperture, said axially rotatable cylinder having a coupling socket formed in its upper end for driving engagement with said electric actuator mechanism: and a tubular slide slidably disposed about said sleeve and carrying a pill pin for slidably engaging pills and/or capsules disposed in said helical indented groove as said electric actuator mechanism causes said axially rotatable cylinder to rotate and dispense pills and/or capsules out of said pill dispensing opening.

3. A tamper-resistant pill and/or capsule dispenser for attachment to an electronic control and communication unit including inter alia, an electric actuator mechanism, a microprocessor, a graphical user interface and a communications unit, the dispenser including sensors operative under control of said electronic control and communication unit to monitor and dispense prescribed dosages of medications or vitamin supplements in pill and/or capsule form and help control, track and maintain a record of pills and/or capsules dispensed to a patient to ensure that the dispensed product is not improperly removed from or replaced in the dispenser, said dispenser comprising:

a generally rectangular housing having an open top, and a generally closed bottom, except for a pill dispensing opening formed in a lower side portion of the rectangular housing;

a plurality of idler rollers disposed at various locations within said housing;

a Geneva drive and sprocket disposed within and affixed to said housing in predetermined locations relative to said idler rollers;

a closed loop pill ring chain formed by pill carrying rings linked together to form a serpentine pattern mounted about said Geneva drive and sprocket as well as the several idler rollers, said serpentine path passing directly over said pill dispensing opening; and a cover plate affixed to and forming a closure for said housing, said cover plate having an elongated opening disposed to lie over the serpentine path traversed by said closed loop pill ring chain and forming a pill fill access slot and including a fill access cover;

whereby the electric actuator mechanism is linked to said Geneva drive so as to cause said pill ring chain to intermittently pause with one of said pill carrying rings lying directly over said pill dispensing opening to dispense one or more pills and/or capsules therefrom.

* * * * *